United States Patent
McFall et al.

(10) Patent No.: US 6,183,587 B1
(45) Date of Patent: *Feb. 6, 2001

(54) METHOD OF MAKING SANITARY NAPKIN COMPRISING THREE DIMENSIONALLY SHAPED TUBE OF ABSORBENT MATERIAL

(75) Inventors: Ronald Ray McFall, West Chester; John Lee Hammons, Hamilton; Diana Lynn Gann, Lebanon; John Richard Noel, Cincinnati, all of OH (US)

(73) Assignee: The Procter & Gamble Company, Cincinnati, OH (US)

( * ) Notice: Under 35 U.S.C. 154(b), the term of this patent shall be extended for 0 days.

This patent is subject to a terminal disclaimer.

(21) Appl. No.: 09/067,197

(22) Filed: Apr. 27, 1998

Related U.S. Application Data

(63) Continuation-in-part of application No. 08/979,979, filed on Nov. 26, 1997, now Pat. No. 5,928,452, which is a continuation-in-part of application No. 09/027,039, filed on Feb. 20, 1998, and a continuation-in-part of application No. 09/027,379, filed on Feb. 20, 1998.

(51) Int. Cl.[7] ............................. B32B 31/00; A61F 13/15
(52) U.S. Cl. ..................... 156/201; 156/73.1; 156/202; 156/204; 156/216; 156/227; 156/269; 156/270; 156/290; 156/292; 156/308.2; 156/308.4; 604/367; 604/385.01
(58) Field of Search ............................. 604/385.1, 378, 604/383, 367, 385.01; 156/227, 201, 204, 202, 216, 256, 269, 270, 73.1, 308.2, 308.4, 290, 292; 225/97, 103, 104

(56) References Cited

U.S. PATENT DOCUMENTS

H1454   6/1995  Cucuzza et al. ............... 604/385.02

(List continued on next page.)

FOREIGN PATENT DOCUMENTS

| 1318465 | 6/1993 | (CA) . |
| 0162451 | 11/1985 | (EP) . |
| 0299532 | 1/1989 | (EP) . |
| 0335252 | 10/1989 | (EP) . |
| 0335253 | 10/1989 | (EP) . |
| 0357000 | 3/1990 | (EP) . |
| 0525778 | 2/1993 | (EP) . |
| 0750896 | 1/1997 | (EP) . |
| 0768070 | 4/1997 | (EP) . |

(List continued on next page.)

OTHER PUBLICATIONS

U.S. application No. 09/027,039, McFall et al., filed Feb. 20, 1998.
U.S. application No. 09/027,379, McFall et al., filed Feb. 20, 1998.

*Primary Examiner*—Linda L. Gray
(74) *Attorney, Agent, or Firm*—Ingrid N. Hickman; Matthew P. Fitzpatrick; Kevin C. Johnson

(57) ABSTRACT

The method of making a shaped tube of absorbent material for the sanitary napkin, in one embodiment, involves the steps of: (a) providing a web of absorbent material, the web of absorbent material having a length, a width, a longitudinal centerline oriented in the direction of the length of the web of absorbent material, a first surface and an opposed second surface; (b) providing a cover for the first and second surfaces of the web of absorbent material; (c) at least partially covering the first and second surfaces of the web of absorbent material with the cover to form a composite web having longitudinal side margins; (d) folding the composite web at least once with folds defining fold lines that are arranged about the longitudinal centerline of the web of absorbent material; and (e) autogenously bonding a portion of the cover that covers the first surface of the web of absorbent material to a portion of the cover that covers an opposing portion of the second surface of the web of absorbent material.

8 Claims, 15 Drawing Sheets

U.S. PATENT DOCUMENTS

| | | | |
|---|---|---|---|
| 24,137 | 5/1859 | Jacks | 278/73 |
| 238,372 | 3/1881 | Evans | 524/257 |
| 2,331,355 | 10/1943 | Strongson | 604/365 |
| 2,747,575 | 5/1956 | Mercer | 604/385.01 |
| 3,183,909 | 5/1965 | Roehr | 604/385.01 |
| 3,528,422 | 9/1970 | Hodas | 604/374 |
| 3,973,567 | 8/1976 | Srinivasan et al. | 604/385.05 |
| 4,095,542 * | 6/1978 | Hirschman | 112/476.06 |
| 4,196,562 | 4/1980 | Hirschman | 53/450 |
| 4,333,463 | 6/1982 | Holtman | 604/368 |
| 4,340,058 | 7/1982 | Pierce et al. | 604/385.05 |
| 4,425,130 | 1/1984 | DesMarais | 604/389 |
| 4,430,148 | 2/1984 | Schaefer | 156/580.2 |
| 4,433,972 | 2/1984 | Malfitano | 604/385.01 |
| 4,490,147 | 12/1984 | Pierce et al. | 604/378 |
| 4,556,146 | 12/1985 | Swanson et al. | 206/440 |
| 4,639,254 | 1/1987 | LeGault et al. | 604/385.21 |
| 4,673,403 | 6/1987 | Lassen et al. | 604/385.17 |
| 4,758,240 | 7/1988 | Glassman | 604/379 |
| 4,765,477 | 8/1988 | Froidh et al. | 206/438 |
| 4,781,712 | 11/1988 | Barabino et al. | 604/385.201 |
| 4,823,783 | 4/1989 | Willhite, Jr. et al. | 602/52 |
| 4,846,824 | 7/1989 | Lassen et al. | 604/385.17 |
| 4,848,572 | 7/1989 | Herrera | 206/440 |
| 4,854,984 | 8/1989 | Ball et al. | 156/73.5 |
| 5,007,906 | 4/1991 | Osborn, III et al. | 604/385.23 |
| 5,071,414 | 12/1991 | Elliot | 604/385.13 |
| 5,088,993 | 2/1992 | Gaur | 604/385.02 |
| 5,171,302 | 12/1992 | Buell | 604/385.23 |
| 5,181,610 | 1/1993 | Quick et al. | 206/447 |
| 5,197,959 | 3/1993 | Buell | 604/385.23 |
| 5,401,267 | 3/1995 | Courture-Dorschner | 604/384 |
| 5,413,568 | 5/1995 | Roach et al. | 604/358 |
| 5,462,166 | 10/1995 | Minton et al. | 206/440 |
| 5,484,636 | 1/1996 | Berg, Jr. et al. | 428/41.8 |
| 5,518,801 | 5/1996 | Chappell et al. | 428/152 |
| 5,545,156 | 8/1996 | DiPalma et al. | 604/385.23 |
| 5,569,228 | 10/1996 | Byrd et al. | 604/385.02 |
| 5,569,230 | 10/1996 | Fisher et al. | 604/385.06 |
| 5,672,165 | 9/1997 | Belecky et al. | 604/383 |
| 5,674,214 | 10/1997 | Visscher et al. | 604/385.12 |
| 5,827,258 * | 10/1998 | McFall et al. | 604/385.1 |
| 5,928,452 * | 7/1999 | McFall et al. | 156/269 |
| 5,944,706 * | 8/1999 | Palumbo et al. | 604/368 |
| 5,957,906 * | 9/1999 | Roe et al. | 604/378 |

FOREIGN PATENT DOCUMENTS

| | | |
|---|---|---|
| 0891759 | 1/1999 | (EP) . |
| 2153779 | 8/1985 | (GB) . |
| 2191098 | 12/1987 | (GB) . |
| 60-34272 | 10/1985 | (JP) . |
| 63-23080 | 6/1988 | (JP) . |
| 3-118727 | 6/1991 | (JP) . |
| 5-18523 | 3/1993 | (JP) . |
| 5-68517 | 9/1993 | (JP) . |
| 6-75446 | 10/1994 | (JP) . |
| 6-315504 | 11/1994 | (JP) . |
| 7-27537 | 5/1995 | (JP) . |
| 7-28527 | 5/1995 | (JP) . |
| 7-33315 | 6/1995 | (JP) . |
| 7-39820 | 7/1995 | (JP) . |
| 8-224269 | 9/1996 | (JP) . |
| 9-220255 | 8/1997 | (JP) . |
| 9-253127 | 9/1997 | (JP) . |
| 9-313529 | 9/1997 | (JP) . |
| 9-266928 | 10/1997 | (JP) . |
| 9-38132 | 10/1997 | (JP) . |
| 2789242 | 8/1998 | (JP) . |
| 89/02729 | 4/1989 | (WO) . |
| 91/18574 | 12/1991 | (WO) . |
| 93/11725 | 6/1993 | (WO) . |
| 94/16658 | 8/1994 | (WO) . |
| 96/05790 | 2/1996 | (WO) . |
| 96/26699 | 9/1996 | (WO) . |
| 97/45082 | 12/1997 | (WO) . |
| WO 99/26769 | 3/1999 | (WO) . |

* cited by examiner

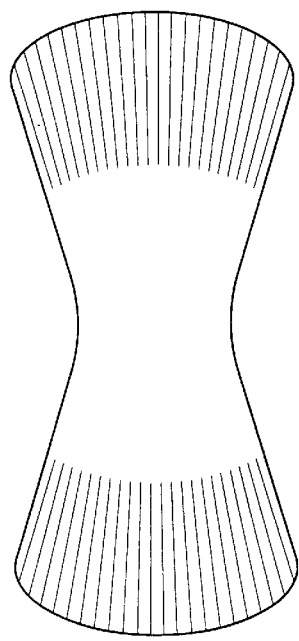
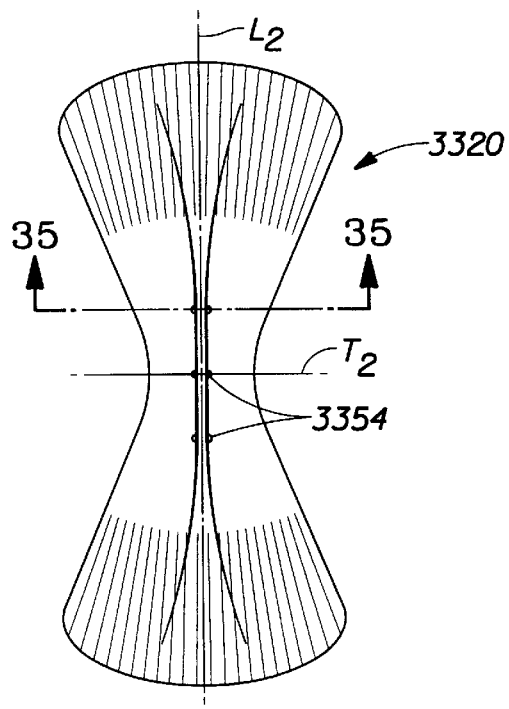
Fig. 33    Fig. 34
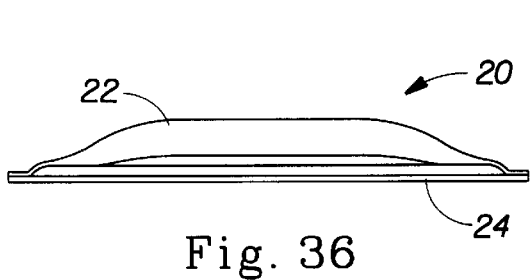
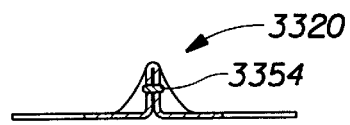
Fig. 36    Fig. 35
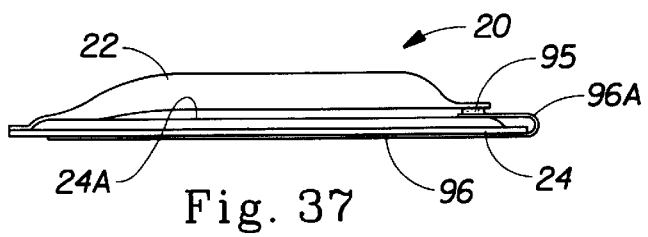
Fig. 37
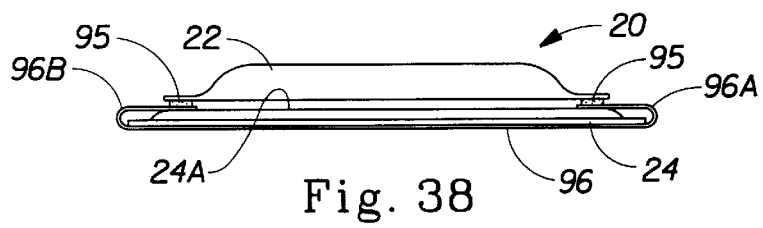
Fig. 38

US 6,183,587 B1

METHOD OF MAKING SANITARY NAPKIN COMPRISING THREE DIMENSIONALLY SHAPED TUBE OF ABSORBENT MATERIAL

This application is a continuation-in-part of the following patent applications: Ser. No. 08/979,979, filed on Nov. 26, 1997 (now U.S. Pat. No. 5,928,452); Ser. No. 09/027,039, filed on Feb. 20, 1998 (pending); and Ser. No. 09/027,379, filed on Feb. 20, 1998 (pending).

FIELD OF THE INVENTION

The present invention relates to a sanitary napkin comprising a three dimensionally-shaped tube of absorbent material and a method of making the same. A method of individually packaging a three dimensionally-shaped absorbent article is also described.

BACKGROUND OF THE INVENTION

Absorbent articles such as sanitary napkins, pantiliners, disposable diapers, incontinence products, and bandages are designed to absorb and retain liquid and other discharges from the human body and to prevent body and clothing soiling.

A need that occurs in the manufacture of absorbent articles is to provide the absorbent article with more complex three dimensional shapes in an effort to more closely fit the wearer's body. In the past, a number of efforts were made to create body-conforming articles.

One way to provide an absorbent article with a body-conforming shape, for instance a triangular cross-section for a sanitary napkin, was often to stack elements on top of one another. Examples of such structures are shown in U.S. Pat. No. 4,340,058 issued to Pierce, et al. on Jul. 20, 1982, and U.S. Pat. No. 4,490,147 issued to Pierce, et al. on Dec. 25, 1984. Stacking materials to form three dimensionally-shaped absorbent articles suffers from the drawback that it is very difficult to carry out on high speed manufacturing processes. This is due to difficulties encountered with registration and differences in extensibility of the materials (which are usually supplied in continuous form) that are stacked. That is, it is difficult to maintain such materials in the precise degree of alignment with respect to each other that is necessary for stacking. If continuous webs have different cross-sectional areas, the webs with the smaller cross-sectional area will tend to stretch more in such a process under the same amount of force than will webs having a larger cross-sectional area.

Other efforts involved molding the absorbent article, or an element thereof into a body-conforming shape. One such effort is described in U.S. Pat. No. 5,197,959 entitled "Absorbent Article" issued to Buell on Mar. 30, 1993. The search for improved body-conforming absorbent articles, and methods for making the same, has continued.

Thus, a need exists for absorbent articles with complex, body-fitting shapes that do not involve stacking elements of various shapes different from the shape desired, or molding an element, in order to form an absorbent article of the desired shape.

SUMMARY OF THE INVENTION

The present invention is directed to an absorbent article comprising a three dimensionally-shaped tube of absorbent material and a method of making the same.

In one preferred embodiment, the absorbent article is a compound sanitary napkin. The compound sanitary napkin comprises a base pad having a body-facing side, a garment-facing side, and a longitudinal centerline. The base pad preferably comprises a liquid pervious topsheet, a liquid impervious backsheet joined to the topsheet, and an absorbent core positioned between the topsheet and the backsheet. A tube of absorbent material is positioned on the body-facing side of the base pad and is aligned along the longitudinal centerline of the base pad.

The tube of absorbent material preferably comprises an absorbent material and a cover at least partially wrapping the absorbent material. The absorbent material is preferably penetrated by autogenous bonds that join one portion of the cover to an opposing portion of the cover to provide the tube with a unique three dimensional shape. In a particularly preferred embodiment, the tube of absorbent material has a tri-lobal cross-sectional configuration, at least in the center of the sanitary napkin. The tri-lobal cross-sectional configuration comprises an inverted "T"-shaped cross-section comprising an upright central lobe symmetrically disposed about the longitudinal centerline and two outer lobes. The central lobe has a greater caliper than the two outer lobes, and is preferably capable of fitting comfortably in the space between the wearer's labia majora and minora.

The present invention is also directed to a method of making a shaped tube of absorbent material for the sanitary napkin described above. The method preferably comprises the steps of:

(a) providing a web of absorbent material, the web of absorbent material having a length, a width, a longitudinal centerline oriented in the direction of the length of the web of absorbent material, a first surface and an opposed second surface;

(b) providing a cover for the first and second surfaces of the web of absorbent material;

(c) at least partially covering the first and second surfaces of the web of absorbent material with the cover to form a composite web having longitudinal side margins;

(d) folding the composite web at least once with folds defining fold lines that are arranged about the longitudinal centerline of the web of absorbent material; and (e) autogenously bonding a portion of the cover that covers the first surface of the web of absorbent material to a portion of the cover that covers an opposing portion of the second surface of the web of absorbent material.

In particularly preferred versions of the method of the present invention, the web of absorbent material comprises an absorbent foam material. The absorbent foam material preferably comprises a high internal phase emulsion (or "HIPE") foam. The web of absorbent foam material is preferably formed into a plurality of particles of foam. In a preferred embodiment, this occurs between the step (c) of at least partially covering the first and second surfaces of the web of absorbent material with the cover to form a composite web, and the step (d) of folding the composite web at least once.

The step (d) of folding the composite web at least once may further comprise: (i) folding the longitudinal side margins of the composite web inward toward the longitudinal centerline about a first set of longitudinally-oriented folding lines to form a C-folded structure; and then (ii) folding the composite web inward about the longitudinal centerline so that the longitudinal side margins of the folded composite web are brought adjacent to each other.

The bonded and shaped tube of absorbent material is joined to a base pad to form a compound sanitary napkin. In some embodiments, the ends of the tube of absorbent material are splayed out before the tube of absorbent material is attached to the base pad to provide the tube with a more pronounced profiled shape.

Numerous alternative embodiments and features for the absorbent article are included within the scope of the present invention. A method of individually packaging a three dimensionally-shaped absorbent article is also described.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

FIG. 33 is a plan view of a composite web of absorbent material that is mechanically strained so that it is formed into an hourglass shaped configuration.

FIG. 34 is a plan view of the composite web of absorbent material shown in FIG. 33 after the composite web has been gathered inward and secured so that a longitudinally-oriented hump is formed down the center of the composite web.

FIG. 35 is a cross-sectional view of the composite web of absorbent material shown in FIG. 34 taken along line 35—35 of FIG. 34.

FIG. 36 is a schematic side view of a compound sanitary napkin in which the ends of the tube of absorbent material are joined to the base pad, and the portion of the tube between its ends are not joined to the base pad.

FIG. 37 is a schematic side view of a compound sanitary napkin in which one end of the tube of absorbent material is permanently attached to the base pad, and the other end is releasably attached to the base pad.

FIG. 38 is a schematic side view of a compound sanitary napkin in which both ends of the tube of absorbent material are releasably attached to the base pad.

DETAILED DESCRIPTION OF THE INVENTION

The present invention relates to an absorbent article comprising a three dimensionally-shaped tube of absorbent material and a method of making the same. In one preferred embodiment, the absorbent article comprises a compound sanitary napkin, and the tube of absorbent material provides the compound sanitary napkin with the desired body-conforming shape.

1. Overall Characteristics of the Sanitary Napkin.

The term "sanitary napkin", as used herein, refers to an article which is worn by females adjacent to the pudendal region that is intended to absorb and contain the various exudates which are discharged from the body (e.g., blood, menses, and urine). The term "compound sanitary napkin", as used herein, refers to a sanitary napkin comprised of separate constituents joined to one another to form a unitary structure.

Figure 1:
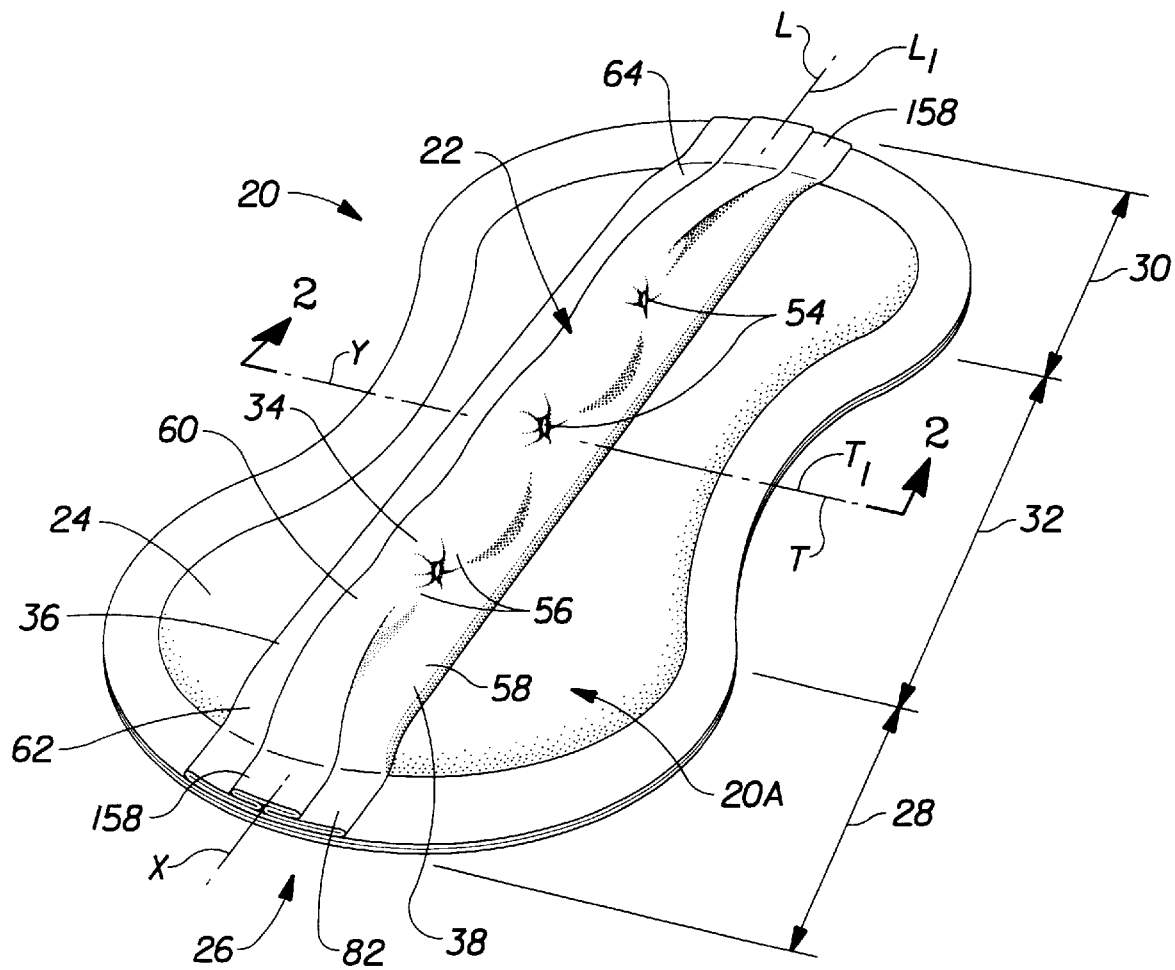
FIG. 1 is a perspective view of a compound sanitary napkin having a tube of absorbent material on the body-facing side thereof, which is provided with one three dimensional shape.
Figure 2:
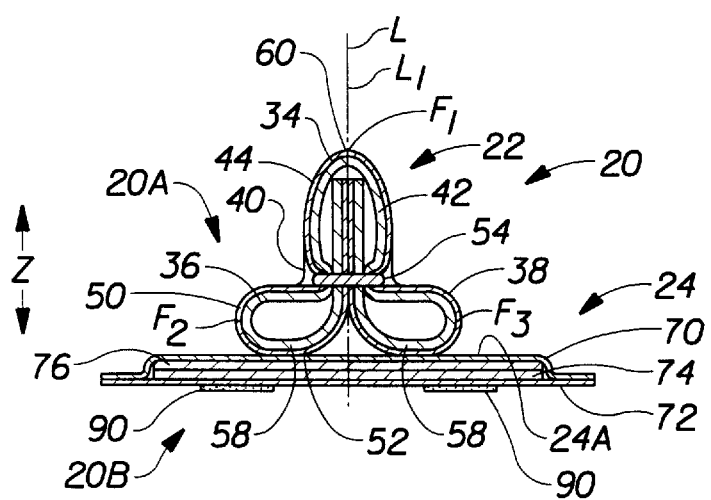
FIG. 2 is a schematic cross-sectional view of the compound sanitary napkin shown in FIG. 1, taken along lines 2—2.

FIGS. 1 and 2 show one preferred embodiment of a compound sanitary napkin 20 according to the present invention. The compound sanitary napkin 20 comprises a primary menstrual pad (the tube of absorbent material) which is joined to a panty protector (or "base pad"). The compound sanitary napkin 20 comprises a longitudinally-oriented tube of absorbent material 22 having a three dimensionally-shaped structure that is is joined to one of the surfaces of the base pad 24.

The sanitary napkin 20 and the base pad 24, each have a body-facing surface and a garment-facing surface. The body-facing surface or "body surface" of the sanitary napkin is designated 20A and the garment surface of the sanitary napkin is designated 20B. The body surface of the base pad 24 is designated 24A, and the garment surface is designated 24B. The sanitary napkin 20 is shown in FIG. 1 as viewed from its body surface 20A. The body surface 20A is intended to be worn adjacent to the wearer's body. The garment surface 20B is intended to be placed adjacent to the wearer's undergarments when the sanitary napkin 20 is worn.

The sanitary napkin 20 has two centerlines, a principal longitudinal centerline L and a principal transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction.

The tube of absorbent material 22 also has two centerlines, a longitudinal centerline $L_1$ and a transverse centerline $T_1$. The tube of absorbent material 22 is preferably joined to the base pad 24 so that the longitudinal centerline $L_1$ of the tube of absorbent material 22 is aligned with the principal longitudinal centerline of the sanitary napkin 20. The transverse centerline $T_1$ of the tube of absorbent material 22 may also be aligned with the principal transverse centerline $T_1$ of the sanitary napkin 20 as shown in FIG. 1. In other embodiments, however, the transverse centerline $T_1$ of the tube of absorbent material 22 may be offset either forward or rearward of the principal transverse centerline T.

The base pad 24 (and the sanitary napkin 20) has a first (or front) end region 28, a second (or rear) end region 30, and a central region 32 positioned between the first and second end regions. The end regions 28 and 30 extend outwardly in the longitudinal direction from the edges of the central region 32 about ⅛ to about ⅓, or more, of the length of the main body portion. The term "main body portion" refers to the portion of the sanitary napkin exclusive of any laterally extending flaps that may optionally be provided thereon. (In the embodiment shown in FIG. 1, the main body portion comprises the base pad 24 and the tube of absorbent material 22.) A detailed description of the characteristics of a central region and two end regions for a sanitary napkin is contained in U.S. Pat. No. 4,690,680 issued to Higgins on Sep. 1, 1987.

The characteristics of the sanitary napkin 20 may be further described in terms of a Cartesian coordinate system. For the purpose of this description, the X axis runs along the principal longitudinal centerline L, of the sanitary napkin 20. The Y axis runs along the principal transverse centerline, T, of the sanitary napkin 20. The X-Y plane is a plane generally parallel to the faces of the base pad 24. The Z-direction is perpendicular to the X-Y plane.

A. The Three Dimensionally-Shaped Tube of Absorbent Material.

The three dimensional aspects of the tube of the absorbent material can include, but are not limited to the following features which are described in greater detail below: the fact that one portion of the tube of absorbent material is segregated from another portion or portions thereof; the profiling of the tube of absorbent material; the lobes of the tube of absorbent material; and the indentations or tufted regions formed in the tube of absorbent material.

The tube of absorbent material 22 can have a number of different three dimensional shapes. In the preferred embodiment shown in FIG. 2, the tube of absorbent material 22 can be described as having an inverted "T"-shaped cross-section, or more specifically, a "tri-lobal" cross-sectional configuration in the central region 32 of the sanitary napkin 20. As shown in FIG. 2, the tri-lobally shaped tube comprises a central lobe 34 and two outer lobes 36 and 38. The tube of absorbent material 22 is joined to the body surface 24A of the base pad 24. As shown in FIG. 2, the central lobe 34 is preferably symmetrically disposed about the principal longitudinal centerline L of the sanitary napkin 20. The central lobe 34 preferably has a greater caliper than the outer lobes 36 and 38. The outer lobes are also preferably symmetrically disposed about the principal longitudinal centerline L of the sanitary napkin 20 and have the same caliper as each other.

The central lobe 34 is preferably capable of achieving comfortable, conforming interlabial fit (i.e., fit in the space between a female wearer's labia majora and minora). The central lobe 34 and outer lobes 36 and 38 may be of any suitable size that allows this to occur. The central lobe 34 preferably has a caliper (or Z-direction height (first caliper)) in the range of between about 7 mm to about 25 mm measured from the body-facing surface 24A of the base pad 24. The outer lobes 36 and 38 preferably have a caliper (second caliper) in the range of between about 2 mm to about 10 mm measured from the body-facing surface of the base pad. The above calipers of the central lobe 34 and outer lobes 36 and 38 are measured under a confining pressure of 0.06 psi. (350 Pa). The base pad 24 preferably defines a third caliper of the overall compound sanitary napkin 20, and the third caliper is preferably less than the first and second calipers.

The compound sanitary napkin of the present invention differs from prior compound sanitary napkins having tubes of absorbent material with a circular or oval cross-sectional configuration. In the case of some wearers of the compound sanitary napkin of the present invention, substantially the entire tube of absorbent material can fit within the interlabial space (along at least one section along the length of the tube) with no action on the part of the wearer to place it there.

Figure 8A:
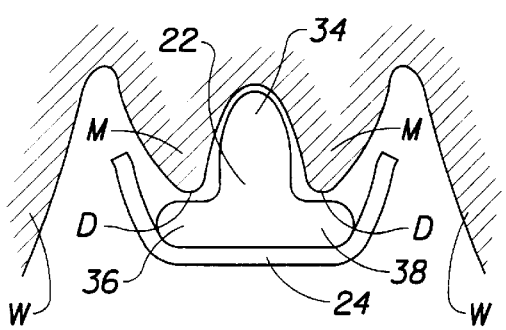
FIG. 8A is a schematic cross-section taken through a part of the wearer's body that shows one example of how the three dimensional tube of absorbent material may fit relative to the space between the wearer's labia.
Figure 8:
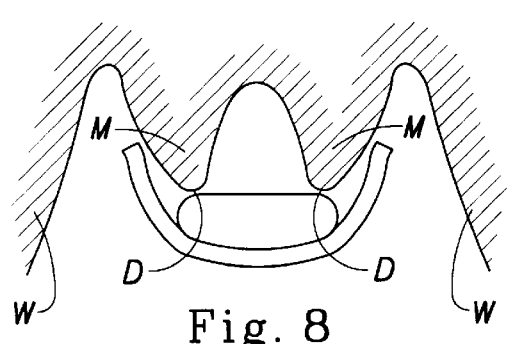
FIG. 8 is a schematic cross-section taken through a part of the wearer's body that shows how a prior art compound sanitary napkin may fit relative to the space between the wearer's labia.

FIG. 8 is a schematic cross-section taken through the relevant part of the wearer's body that shows how a prior art compound sanitary napkin having a tube with a circular or an oval cross-section may fit relative to the space between the wearer's labia. In FIG. 8, the wearer's legs are designated by reference letter W, the labia majora is designated by reference letter M, and for the purposes of this specification only, the distal surfaces of the labia majora are designated by reference letter D. In some embodiments, the tubes having a circular or oval cross-sectional configurations may achieve a degree of interlabial fit.

As shown in FIG. 8A, the interlabial fit that the three dimensionally-shaped tube of absorbent material 22 of the sanitary napkin 20 of the present invention is capable of achieving, is much greater than that previously obtainable with sanitary napkins having tubes of circular or oval cross-sectional configurations. The tube of absorbent material 22 of the sanitary napkin 20 of the present invention penetrates much further into the interlabial space and achieves much better conformity with this region of the wearer's body. The tube of absorbent material 22 is preferably also highly resilient under wet and dry conditions so that it dynamically adjusts and conforms to changes in the shape of the interlabial space and does not collapse when subjected to pressure and/or when it is wetted by bodily exudates.

Figure 8B:
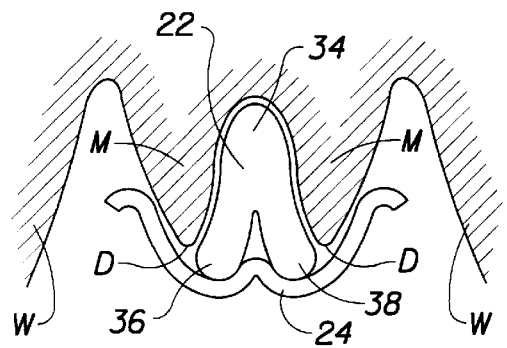
FIG. 8B is a schematic cross-section taken through a part of the wearer's body that shows another example of how the three dimensional tube of absorbent material may fit relative to the space between the wearer's labia.

The tri-lobal cross-section is advantageous in that the outer lobes 36 and 38 provide additional absorbent material to supplement the absorbent material provided by the interlabially-conforming central lobe 34. The outer lobes 36 and 38 may stay in substantially the same relationship to the central lobe 34 and lie outside of the wearer's interlabial space as shown in FIG. 8A and intercept bodily exudates as they leave the wearer's body. The outer lobes 36 and 38 provide additional surface area adjacent to the distal surfaces, D, of the labia majora M, for intercepting exudates discharged from the wearer's body. In the case of some wearers, however, as shown in FIG. 8B, the outer lobes 36 and 38 can converge and form a narrower structure in which they also fit at least partially interlabially. As shown in FIG. 8B, in some wearers, this narrower structure is capable of fitting substantially entirely interlabially with the outer lobes also fitting interlabially. Although it is not mandatory that it do so, the tube of absorbent material 22 preferably intercepts most or all of the discharged bodily exudates so that the base pad 24 remains clean and dry.

The tube of absorbent material 22 in the embodiment shown in FIG. 2 is preferably formed from three components. These comprise a topsheet 40, an absorbent material 42, and a containment web 44.

The topsheet 40 may be manufactured from a wide range of materials such as woven and nonwoven materials; polymeric materials such as apertured formed thermoplastic films, apertured or unapertured plastic films, and hydroformed thermoplastic films; porous foams, reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers); bicomponent fibers (that is, fibers having a core of one material which enclosed in a sheath made of another material), or from a combination of natural and synthetic fibers.

In a preferred embodiment, the topsheet 40 comprises an apertured formed film. The topsheet 40 may comprise a formed film such as that described in U.S. Pat. No. 4,637,819 issued to Ouellette, et al. or U.S. patent application Ser. No. 08/442,935 entitled "Fluid Transport Webs Exhibiting Surface Energy Gradients" filed in the name of Ouellette, et al. on May 31, 1995 (PCT Publication WO 96/00548, published Jan. 11, 1996). One especially preferred apertured formed film is described in U.S. Pat. No. 4,342,314 issued to Radel, et al. on Aug. 3, 1982 and U.S. Pat. No. 4,463,045 issued to Ahr, et al. on Jul. 31, 1984 which are marketed on sanitary napkins by The Procter & Gamble Company of Cincinnati, Ohio as the "DRI-WEAVE" topsheet. Preferably, this topsheet material is provided with added softness and flexiblity by forming a pattern into the topsheet material while it is fed through a nip between mating rolls in conjunction with a preferred process of forming the absorbent material into a plurality of particles (described below). It has been found that this process greatly changes the surface appearance and feel of the preferred apertured film topsheet material so that it is virtually no longer recognizable as being the same apertured film, but instead appears to be a "cloth-like","gauze-like", or "cottony" material.

The absorbent material 42 in the tube of absorbent material 22 may be any absorbent material that is capable of absorbing or retaining liquids (e.g., menses and/or urine). The absorbent material 44 in the tube of absorbent material 22 may be a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combination of materials, or mixtures of these.

The absorbent material may also partially comprise less absorbent or nonabsorbent material, such as polyurethane foam, which when combined with absorbent material (such as absorbent gelling materials), can be formed into suitable absorbent structures. Preferred absorbent materials are those in the above list that are wet and dry resilient and/or can be formed into a resilient structure. Particularly preferred absorbent materials can also be chopped into particles in the preferred process of making the tube of absorbent material described below.

The absorbent material in the tube of absorbent material 22 preferably comprises an absorbent foam, preferably a resilient absorbent foam. Some particularly preferred absorbent foam materials are made from high internal phase emulsions, and are known as "HIPE" foams. Suitable HIPE absorbent foams are described in U.S. Pat. No. 5,260,345 issued to DesMarais, et al. on Nov. 9, 1993; U.S. Pat. No. 5,268,224 issued to DesMarais, et al. on Dec. 7, 1993; U.S. Pat. No. 5,387,207 issued to Dyer, et al. on Feb. 7, 1995; U.S. Pat. No. 5,550,167 issued to DesMarais on Aug. 27, 1996; U.S. Pat. No. 5,563,179 issued to Stone, et al. on Oct. 8, 1996; U.S. Pat. No. 5,650,222 issued to DesMarais, et al. on Jul. 22, 1997; and allowed U.S. patent application Ser. No. 08/542,497 filed Oct. 13, 1995, by Dyer, et al. (P&G Case 5546R). These patents may be referred to herein as the "Absorbent Foam Material" patents. Such absorbent foam materials are particularly preferred because they can be provided with good resistance to compression and resiliency following compression. The absorbent foam materials described in these different patents have properties that allow them to acquire and/or store various bodily exudates. They may also be provided with the ability to absorb particular types of bodily exudates (e.g., menses, runny bowel movements, and/or urine). Such materials may have a low tensile strength and/or low structural integrity, which makes them suitable for chopping them into particles.

Figure 50:
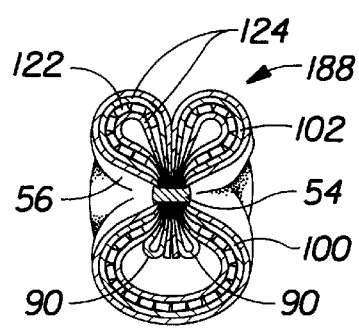
FIG. 50 is a simplified cross-sectional view of the web shown in FIG. 49 taken through one of the bond sites along line 50—50 of FIG. 49.

In particularly preferred embodiments, the absorbent foam material comprises a plurality of particles 48 of absorbent foam. The particles 48 of absorbent foam are best seen in FIG. 50, which is a view of the tube of absorbent material 22 in an inverted condition prior to attachment to the base pad 24. The particles can be in any suitable shape. They may have regular shapes or irregular shapes. Examples of particles having regular shapes are particles in the shape of cubes, three dimensional rectangular particles, prisms, or other parallelepipeds. The particles can all be of the same general size and/or shape, or they can be of varying sizes and/or shapes.

In one preferred embodiment, the particles of absorbent foam material 48 are generally in the configuration of parallelepipeds. When the particles of absorbent foam 48 are described as being "generally" in a particular configuration, it is understood that they need not be exactly in the configuration specified, and that all of the particles 48 need not be exactly in the configuration specified. It is sufficient if some of the particles 48 are roughly in the shape specified so that they are recognizable as having such a shape.

The particles 48 of absorbent foam material can be of any suitable size. The particles preferably have a largest dimension having a nominal size, that is preferably between about 1.0 mm and about 25.4 mm, and more preferably between about 2 mm and about 16 mm. However, particles as small as 0.5 mm and smaller, and particles larger than about 25.4 mm are also contemplated. Particles having a nominal size of about 1.0 mm or greater are those which are generally retained on the surface of a U.S. Standard No. 18 mesh sieve screen. Particles having a nominal size of less than about 25.4 mm are those which generally pass through a U.S. Standard 25.4 mm sieve screen. In one preferred embodiment, the particles 48 are rectangular prisms or parallelepipeds that are about 1.5 mm×1.5 mm×2 mm. The particles of absorbent foam material 48 can all be of a relatively uniform size, or they can be of varying particle sizes. In the preferred embodiment shown, they are of a relatively uniform particle size.

The use of particles of absorbent material provides a number of advantages. The particles of absorbent foam material 48 provide the tube of absorbent material 22 with a resilient "bean bag" like structure that allows for better conformation to the shape of this region of the wearer's body than do webs or sheets of absorbent materials. The use of particles of foam is also believed to make the tube of absorbent material 22 softer, and more comfortable to wear. It should be understood, however, that making the tube of absorbent material 22 partially, or entirely, from absorbent material comprising sheets or web(s) of absorbent material such as absorbent foam is also within the scope of the present invention.

The particles of absorbent foam material 48 are preferably held in place inside the containment web 44. The containment web 44 can be any suitable material that is capable of containing the particles of absorbent foam material 48. For the preferred embodiment described herein, the containment web 44 should also be capable of being utilized as a carrier web in the process of forming the absorbent foam material into particles as described in greater detail below. The containment web 44 can be made from a wide range of materials such as woven and nonwoven materials; polymeric materials such as apertured formed thermoplastic films, apertured or unapertured plastic films, and hydroformed thermoplastic films; porous foams, reticulated foams; reticulated thermoplastic films; and thermoplastic scrims. Particularly preferred materials for use as the containment web are described in greater detail in conjunction with the method of making the tube of absorbent material 22.

In one preferred embodiment, as will be discussed in greater detail below, the containment web 44 comprises a web of material, such as a nonwoven web that is wrapped around the particles of foam absorbent material 48 to form a composite web 50. In particularly preferred embodiments, the composite web 50 is thereafter folded (preferably longitudinally) in at least one place to provide the tube of absorbent material 22 with a distinct three dimensional shape. (Folding the composite web 50 provides greater flexibility in the number of three-dimensionally shaped structures into which the composite web 50 can be formed.)

The containment web 44 provides a number of advantages. One primary advantage is that contains the particles 48 within the boundaries of the containment web 44 so that the composite web 50 can be folded or otherwise manipulated. Because of this, the particles 48 will stay in the same relationship relative to the adjacent portions of the containment web 44, rather than falling into a loose mass of particles at the lowest point of the folded composite web 50.

The components of the tube of absorbent material 22 can be joined together if desired. Alternatively, one or more of these components need not be joined to the adjacent component or components. In a preferred embodiment, the topsheet 40 and the containment web 44 are joined together to form a composite topsheet, and the composite topsheet is joined to the absorbent material. If these components are joined, they can be joined together in any suitable manner, such as by adhesives. Preferably, they are joined by a spiral pattern of adhesives. A preferred adhesive for this purpose is a hydrophilic adhesive known as Findley adhesive #4111 obtained from Findley Adhesives of Wauwatosa, Wis. Preferably, as described in greater detail in the section of this specification that deals with the method of making the shaped tube of absorbent material, these components are also integrated together by passing them through a nip between one or more pairs of mating rolls in conjunction with a preferred process of forming the absorbent material 42 into a plurality of particles.

The composite web 50 can be folded into any suitable structure. The composite web 50 can be folded (and thereafter bonded) to form structures having a wide variety of cross-sectional configurations. The cross-sectional configuration of the tube of absorbent material 22 can be uniform along the length of the tube or it can vary along the length of the tube of absorbent material 22. The composite web 50 can be folded to provide a structure that is profiled (or contoured) along its length, profiled in width (in the transverse direction), and/or profiled in height. Providing different cross-sectional configurations along the length of the sanitary napkin, may be used to provide the tube of absorbent material 22 with an optimal shape for body conformation at each place along the length thereof.

To form the preferred tri-lobal embodiment shown in the FIG. 2, the composite web 50 is folded in three places about longitudinally-oriented fold lines. The longitudinal side margins of the composite web are folded inwardly toward the longitudinal centerline of the composite web 50. The composite web 50 is then folded inwardly again about its longitudinal centerline. The fold lines form the composite web 50 into an inverted U-shaped configuration at its top surface and two U-shaped portions along its bottom surface. One of the fold lines $F_1$ (the one which is formed last) forms a ridge on the top surface of the tube of absorbent material. The U-shaped portions along the bottom surface are preferably folded outwardly so that the other two fold lines, $F_2$ and $F_3$ form the lateral side edges of the tube of absorbent material. The folding process is described in greater detail below in conjunction with the method of making the tube of absorbent material 22. It should be understood that it is not necessary for these fold lines to form sharp creases in the composite web 50. Instead, the fold lines preferably impart gradual bends in the composite web 50.

The preferred process of forming the absorbent foam into particulate material (described in greater detail below) is advantageous in that it provides the composite web 50 with additional flexibility to assist the composite web 50 in folding in this manner. If it were not for this additional flexibility, the absorbent foam material 42 may fracture at locations that are undesirable when the composite web 50 is folded. In addition, if not for this additional flexibility, the topsheet 40, the containment web 44, and/or the combined structure 52 comprising the topsheet 40, the absorbent material 42, and the containment web 44 might be under excessive stresses which would make it difficult to fold the combined structure into the desired configuration.

The three dimensionally-shaped tube of absorbent material 22 preferably has at least one, and preferably three, autogenous fusion bonds 54 formed therethrough. A compressed (or "tufted") region 56 surrounds the bonds 54. The bonds 54 secure the folded combined structure 52 in its folded configuration. The portions 58 of the combined structure 52 that are not held together by the bonds 54 can be unfolded (or folded, if desired) and oriented in other directions. The bonds 54 can, thus, be thought of as segregating different portions of the tube of absorbent material 22 to assist in forming a structure with a distinct three dimensional shape. The bonds 54 preferably segregate a first portion of the tube of absorbent material 22, and in the embodiment shown in FIGS. 1 and 2, create an upraised tubular ridge 60. The upraised tubular ridge 60 creates the central lobe of the cross-sectional configuration. In a particularly preferred embodiment, the bonds 54 are located in the portion of the tube of absorbent material 22 that will lie in the central region 32 of the sanitary napkin 20.

The portions 58 of the tube of absorbent material 22 that are not held together by the bonds 54 (the second portion of the tube of absorbent material 22) are folded away from each other at an angle of about 180 relative to each other to form the outer lobes 36 and 38. When viewing the three dimensionally-shaped tube of absorbent material 22 from the outside, such as in FIG. 1, the second portion of the tube of absorbent material 22 has a generally oval cross-sectional configuration. The oval shape has a pair of longer sides and a pair of shorter curved sides, and one of the longer sides is positioned adjacent to the body-facing side 24A of the base pad 24.

Figure 4:
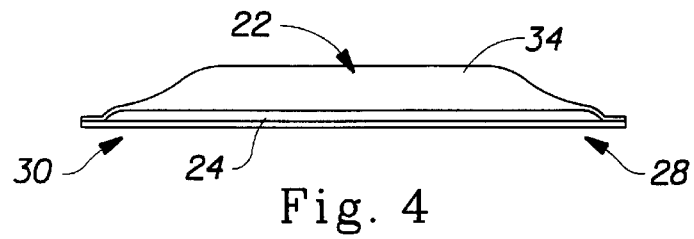
FIG. 4 is a schematic side view of one embodiment of the compound sanitary napkin which shows the profile of the tube of absorbent material.

In the preferred embodiment shown in FIG. 1, the portions 62 and 64 of the tube of absorbent material 22 that will lie in the end regions 28 and 30 of the sanitary napkin are preferably at least slightly flattened and attached to the base pad 24. The tube of absorbent material 22 may, as will be described in greater detail, also be attached to the base pad 24 between its ends 62 and 64. As shown in FIGS. 1 and 4, the tube of absorbent material 22 may be profiled from the front end region 28 of the sanitary napkin 20 to the rear end region 30 of the sanitary napkin. More specifically, the tube of absorbent material 22 has its highest caliper in the center of the sanitary napkin along the transverse centerline, T, and tapers to a lesser caliper at the ends of the sanitary napkin. The bonds 54 form the central lobe 34 where they are present, but do not provide the tube of absorbent material 22 with a central lobe where they are absent.

Figure 5:
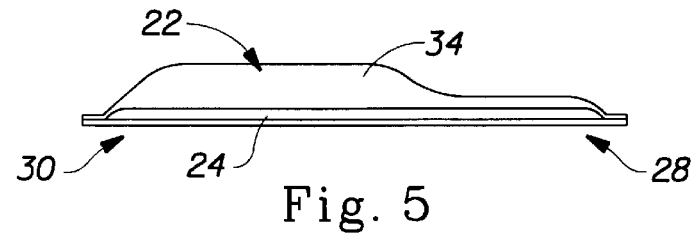
FIG. 5 is a schematic side view of an alternative embodiment of the compound sanitary napkin which has a tube of absorbent material profiled so that the higher caliper central lobe is located primarily over the central region of the base pad and the rear end region.
Figure 6:
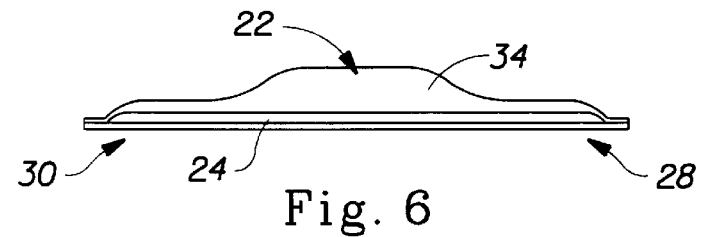
FIG. 6 is a schematic side view of an alternative embodiment of the compound sanitary napkin which has a tube of absorbent material profiled so that the higher caliper central lobe is located primarily over the central region of the base pad.

The bond patterns can be varied to create a tube of absorbent material with increased caliper along all or any portion of the length of the sanitary napkin 20. Several other variations are shown in FIGS. 5 and 6. For example, the bonding can be such that the increased caliper is confined to the central region 32 of the sanitary napkin 20 as shown in FIG. 6. Alternatively, the bond pattern can be used to provide increased caliper in the end regions, or as shown in FIG. 5, in a portion of central region and a portion of the end regions.

B. The Base Pad of the Compound Sanitary Napkin.

The compound sanitary napkin 20, as noted above, comprises a panty protector (or "base pad") 24 and the tube of absorbent material (or "primary menstrual pad") 22 which is placed on top of the base pad 24 and attached thereto at least at the ends of the tube of absorbent material 22.

The base pad 24 can be provided in any suitable configuration and may be constructed from any suitable components. The base pad 24 preferably has generally planar surfaces and is relatively thin. The base pad 24 preferably has a caliper of less than or equal to about 7 mm, more preferably less than or equal to about 5 mm, and most preferably less than or equal to about 3 mm. The base pad 24 preferably comprises an ultra-thin sanitary napkin. Sanitary napkins suitable for use as the base pad 24 include ALWAYS ULTRA sanitary napkins marketed by The Procter & Gamble Company of Cincinnati, Ohio.

The base pad 24 preferably comprises a liquid pervious topsheet 70, a liquid impervious backsheet 72 joined to the topsheet, and an absorbent core 74 positioned between the topsheet 70 and backsheet 72. The base pad 24 may also comprise an optional secondary topsheet 76 that is positioned between the topsheet 70 and the absorbent core 74, or made a part of a composite topsheet. The components of the base pad 24 can be chosen from the same types of materials used as the topsheet, absorbent material, and containment web of the tube of absorbent material 22. Other suitable materials for the components of the base pad 24, and descriptions of the assembly of the same, are contained in U.S. Pat. Nos. 4,950,264, 5,009,653, 5,460,623, and 5,569,231.

In a particularly preferred embodiment, the base pad 24 comprises a variation of such an ALWAYS ULTRA sanitary napkin. This base pad 24 preferably comprises a polyethylene film backsheet 72, an absorbent core 74 comprising a tissue laminate with superabsorbent hydrogel-forming material particles therebetween, and a tissue 76 and a DRI-WEAVE apertured film 70 overlying the absorbent core 74. Suitable tissues are manufactured by Merfin Hygienic Products, Ltd. of Delta, British Columbia, Canada. The tissue 76 overlying the absorbent core 74 is preferably joined to the absorbent core 74 by a spiral pattern of adhesive.

Preferably, the components of the base pad 24 are free of any fusion bonds in this embodiment for greater flexibility. The increased flexibility allows the compound sanitary napkin, and particularly the tube of absorbent material 22 on the same to more easily assume the desired body-conforming configurations shown in FIGS. 8A and 8B. In this particularly preferred embodiment, the base pad 24 also comprises flaps extending laterally outward from its longitudinal side edges. Suitable flaps are described in greater detail below.

C. Relationship Between the Three Dimensionally-Shaped Tube of Absorbent Material and The Base Pad.

Figure 3:
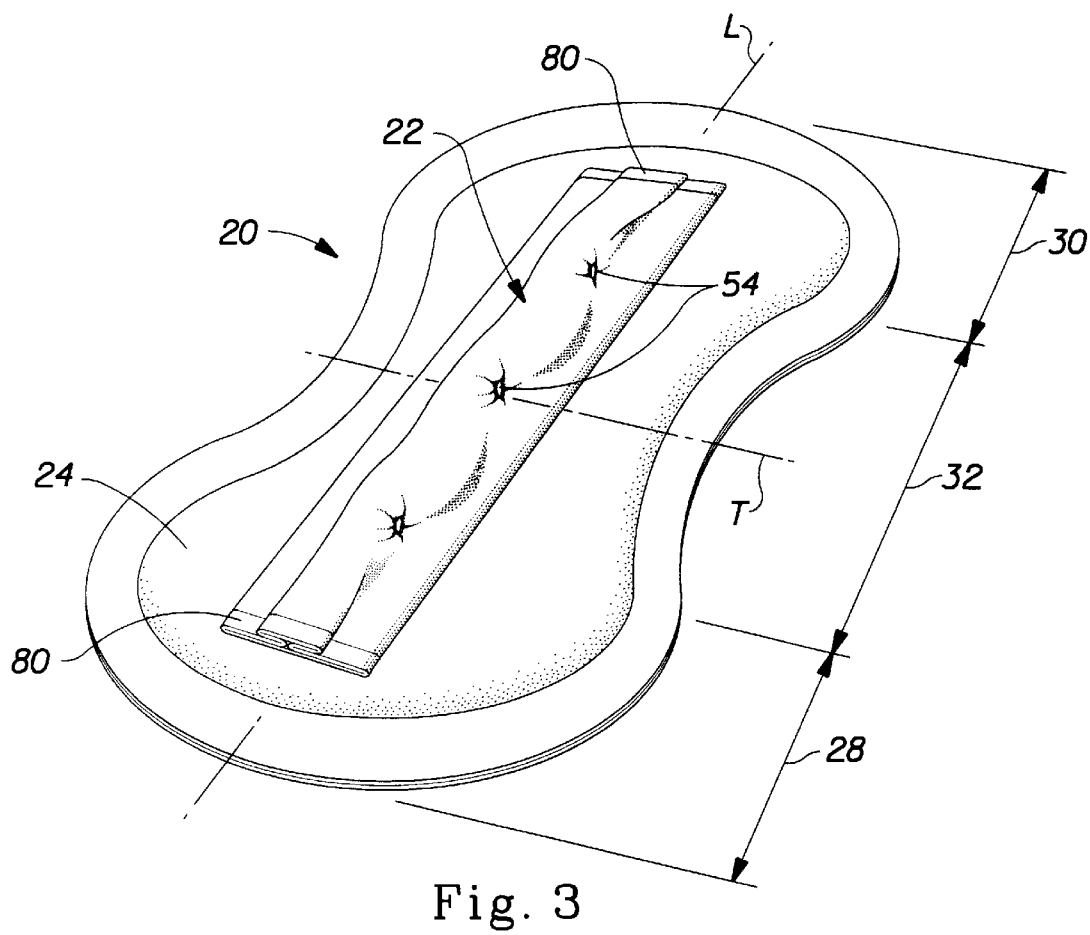
FIG. 3 is a perspective view of a compound sanitary napkin having a tube of absorbent material on the body-facing side thereof, in which the tube of absorbent material is shorter than the base pad.

The tube of absorbent material 22 can be of any suitable length relative to the base pad 24. The tube of absorbent material 22 can be as long as the base pad 24, as shown in FIG. 1. In other embodiments, as shown in FIG. 3, the tube of absorbent material 22 may be shorter than the base pad 24. In these latter embodiments, as shown in FIG. 3, it may be desirable to provide the tube of absorbent material 22 with an anti-wicking end seal 80 at both ends to prevent liquids from wicking out of the ends of the tube of absorbent material 22.

The tube of absorbent material 22 can overlie any suitable portion of the base pad 24. The tube of absorbent material 22 can overlie front end region 28 of the base pad, the rear end region 30 of the base pad, the central region 32, or any portion or portions thereof. In other embodiments, the larger caliper (or height) central lobe 34 of the tube of absorbent material 22 can be shaped to overlie any of these regions of the base pad 24 instead of positioning the entire tube of absorbent material 22 over the selected regions of the base pad 24. FIGS. 4 to 6 show some non-limiting configurations of the tube of absorbent material 22 from the side.

The greater caliper central lobe 34 of the tube of absorbent material described herein is not limited to any particular lengths. In one version of the embodiment shown in FIG. 6, the length may be in the range of about 50 mm to about 100 mm. Such an embodiment may be useful if it is desired to provide the sanitary napkin with a tube of absorbent material 22 in which the central lobe 34, is sufficiently short in length that it fits entirely interlabially.

As discussed above, the tube of absorbent material 22 is joined to the base pad 24. The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. The tube of absorbent material 22 can be joined to the base pad 24 in any suitable manner.

The tube of absorbent material 22 in the embodiment of the compound sanitary napkin shown in FIG. 1 preferably has a topsheet 40 that is longer than the rest of the components of the tube of absorbent material 22 so that there are extensions 158 of the topsheet material at the ends of the tube of absorbent material 22. The attachment of the tube of absorbent material 22 to the base pad 24 is preferably achieved by fusion bonding the extensions 158 of the topsheet material at the ends of the tube to the base pad 24. In some preferred embodiments of such a compound sanitary napkin, there may also be attachment to the base pad 24 between the ends of the tube of absorbent material 22 and the base pad 24. The tube of the compound sanitary napkin can be attached to the base pad between its ends by any suitable attachment means, such as by adhesives.

Figure 7:
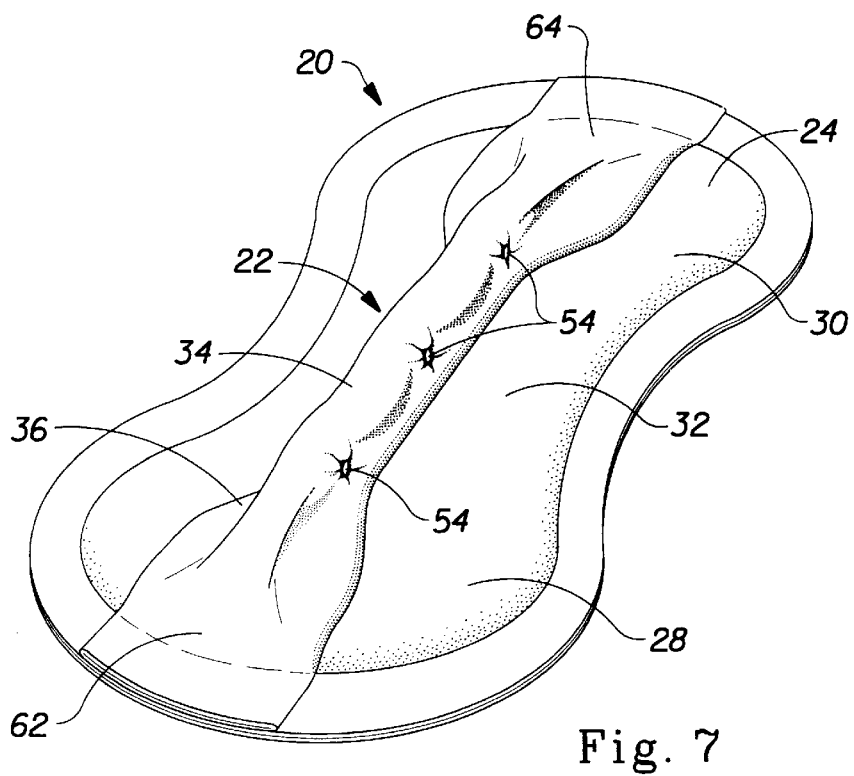
FIG. 7 is a perspective view of a compound sanitary napkin having a tube of absorbent material on the body-facing side thereof, which tube of absorbent material has an alternative three dimensional configuration.

In other embodiments, the tube of absorbent material 22 can be manipulated in a different manner before it is attached to the base pad. For example, FIG. 7 shows an embodiment where the portions 62 and 64 of the tube of absorbent material 22 that will lie in the end regions 28 and 30 of the sanitary napkin are splayed or flared out more dramatically. The tube of absorbent material 22 of the compound sanitary napkin 20 shown in FIG. 7 can be thought of as having a "bow tie" plan view configuration. In this embodiment, the portion of the tube of absorbent material 22 lying in the central region 32 of the sanitary napkin may only have a central lobe 34, and little or no recognizable outer lobes. The portions of the tube of absorbent material lying in the end regions 28 and 30 of the sanitary napkin may be almost completely flattened, having only outer lobes 36 and 38, and little or no recognizable central lobe. This is possible because the portions 62 and 64 of the tube of absorbent material 22 that will lie in the end regions 28 and 30 of the sanitary napkin are not held together by bonds 54.

Additional descriptions of features of compound sanitary napkins and manners of attachment of the components of compound sanitary napkins (although not comprising the technology described herein) are found in P&G's U.S. Pat. No. 4,425,130 entitled "Compound Sanitary Napkin" issued to DesMarais, et al. on Jan. 10, 1984, and in Statutory Invention Registration H1614 entitled "Body Fitting Compound Sanitary Napkin", published in the name of Mayer, et al. on Nov. 5, 1996.

The garment surface 20B of the sanitary napkin 20 may include, and preferably does include, fasteners for attaching the sanitary napkin to the wearer's undergarment. FIG. 2 shows the central pad fastener 90 which is adapted to secure the main body portion of the sanitary napkin to the crotch region of an undergarment. Any types of fasteners known in the art, such as adhesive fasteners and mechanical fasteners can be used as the central pad fastener 90. Fasteners comprising adhesives have been found to work well for this purpose, with pressure-sensitive adhesives being preferred.

D. Packaging and Using the Compound Sanitary Napkin.

Figure 9:
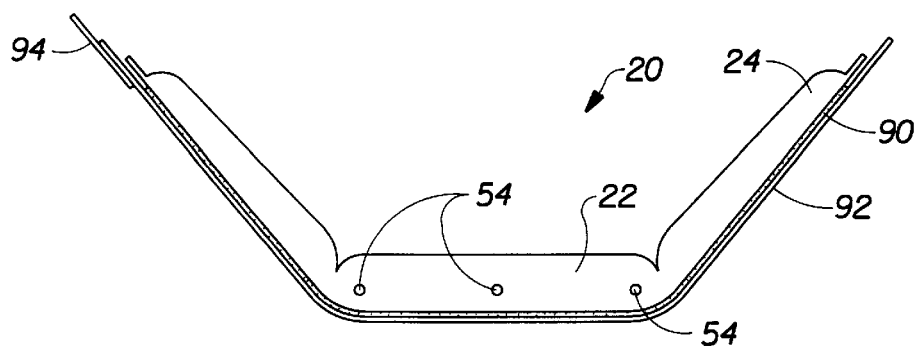
FIG. 9 is a schematic side view of a compound sanitary napkin such as that shown in FIG. 1, which shows how the bonds may provide bending points about which the sanitary napkin can be tri-folded to provide a packaged sanitary napkin.

The compound sanitary napkins described herein are preferably individually packaged. In particularly preferred embodiments, the compound sanitary napkin 20 is individually packaged by tri-folding the same about at least one, and preferably two transverse axes along with a releasable wrapper 92 that is releasably attached to the central pad fastener 90 (as shown in FIG. 9).

A suitable releasable wrapper 92 for this purpose is described in U.S. Pat. No. 4,556,146 issued to Swanson. A particularly preferred releasable wrapper comprises an adhesive fastening system such as that described in U.S. Pat. No. 5,413,568 issued to Roach, et al. and a seal described in U.S. Pat. No. 5,462,166 issued to Minton, et al.

The location of the bonds 54 in the tube of absorbent material 22 is important in the tri-folding process. The transverse axes are preferably located in regions adjacent to or including at least one of the fusion bonds 54 on the tube of absorbent material 22. Preferably, as shown in FIG. 9, the bonds 54 that penetrated the tube of absorbent material 22 are located at or inward of the transverse axes about which the sanitary napkin 20 and wrapper 94 will be folded. As shown in FIG. 9, this assists the tri-folding process by providing bending points about which the tube of absorbent material 22 will fold in a controlled manner. This is particularly useful in folding relatively high caliper components such as the tube of absorbent material 22.

Figure 10:
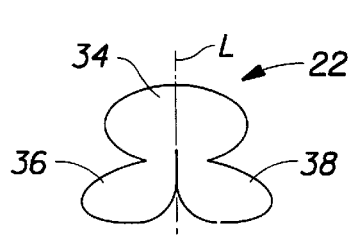
FIG. 10 is a schematic cross-sectional view similar to that of FIG. 2 showing only the tube of absorbent material, which shows how the tri-folding preferably compresses the central lobe of the tube.
Figure 11:
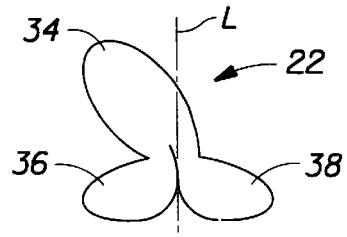
FIG. 11 shows the undesirable tendency for the central lobe to be displaced laterally relative to the longitudinal centerline of the compound sanitary napkin.

Folding the sanitary napkin 20 in such a manner also has the advantage of allowing the position of the central lobe 34 of the tube of absorbent material 22 to be controlled. The tri-folding will involve applying pressure to compress the tube of absorbent material 22. This has the effect of flattening and centering the central lobe 34 of the tube of absorbent material 22 as is shown in FIG. 10. This provides the advantage of making a more compact article for packaging, and consequently, a more compact individually packaged absorbent article. The compression also controls the location of the central lobe 34 and avoids the undesirable tendency for the central lobe 34 to be displaced laterally as shown in FIG. 11.

It should be understood that the method of packaging described herein by folding about bond points on the sides of an absorbent article is not limited to use with compound sanitary napkins. This method can be used with any three dimensionally-shaped absorbent article having a height that defines longitudinal sides in which one or more fusion bonds (or other indentions or indentations) are formed in the longitudinal sides to provide bending axes for folding the absorbent article.

To use the sanitary napkin 20 shown in FIG. 1, the sanitary napkin and wrapper 92 are unfolded and the sanitary napkin 20 is removed from its package. The absorbent foam materials described above are especially preferred for use in the tube of absorbent material 22 because these materials are highly resilient, and will not only provide the benefits described above, but also will rebound substantially entirely to their uncompressed dimensions even after the tube of absorbent material 22 has been highly compressed during packaging and held in a compressed configuration prior to the time the package is opened by the consumer. Preferably, the tube of absorbent material 22 will recover to greater than or equal to: about 50%, more preferably, about 60%, more preferably about 70%, more preferably still about 80%, and most preferably about 90% of its uncompressed caliper.

The sanitary napkin 20 is then placed in the crotch region of the wearer's panties and the central pad adhesive fastener 90 maintains the sanitary napkin 20 in position therein. The panties are then pulled up in the usual manner. The sanitary napkin of the present invention provides advantages over conventional thick sanitary napkins. The sanitary napkin of the present invention provides thickness only where it is needed. The sides of the compound sanitary napkin are flexible and conformable like an ultra thin sanitary napkin. Providing thicker absorbent material in the central region of the sanitary napkin will provide consumers with additional protection and confidence if they are uncomfortable with these aspects of current ultra thin sanitary napkins.

The three dimensionally shaped tube of absorbent material 22 provides the unique advantage that it dynamically adjusts to fit within the wearer's interlabial space without any action on the part of the wearer. The compound sanitary napkin, in some embodiments, can be thought of as having a self-fitting interlabial pad thereon. The preferred tri-lobal cross-section of the tube of absorbent material 22 provides additional surface area to intercept body fluids as shown in FIG. 8A, or forms lobes that converge to fit interlabially as shown in FIG. 8B. Both of these configurations contribute to maintaining the base pad 24 in a clean and dry condition.

Providing the absorbent material in the tube of absorbent material 22 in the form of particles allows the tube of absorbent material to conform to the shape of the wearer's body better than when the absorbent material is in the form of a sheet or web of material. Providing the absorbent material in the tube of absorbent material 22 in the form of particles also makes the tube of absorbent material softer and more comfortable for the wearer.

Providing the bonds 54 in the tube of absorbent material allows the tube of absorbent material to be formed into an optimal shape for body conformity. The bonding, as discussed above, also assists in forming the compound sanitary napkin into a convenient individually packaged article. The process of making the sanitary napkin provides a number of additional benefits. These are described in greater detail below.

E. Alternative Embodiments and Features.

Numerous embodiments of the sanitary napkin of the present invention are also possible.

For example, in one alternative embodiment, the absorbent material in the tube of absorbent material 22 need not be formed into particulate material. That is, a solid piece of absorbent material can be used. However, this may decrease the ability of the tube of absorbent material 22 to conform to the wearer's body. In addition, the formation of fusion bonds through a solid absorbent material, such as an absorbent foam material, will be more difficult, particularly if it is over 4 mm thick. In other embodiments, the absorbent material inside the tube of absorbent material 22 may be in configurations other than particles. For instance, the absorbent material may be in the form of strands, strips, or ribbons of absorbent material.

In any of the foregoing embodiments, or other embodiments, different materials can be employed for the topsheet 40 on the portion of the tube of absorbent material 22 that fits interlabially (the "interlabial portion") of the tube of absorbent material 22. For example, this portion of the tube of absorbent material 22 can comprise nonwoven materials and the remainder of the topsheet 40 can comprise an apertured film. This can provide this portion of the tube of absorbent material with improved comfort. Alternatively, if the topsheet 40 comprises a nonwoven material, the interlabial portion of the topsheet 40 can comprise softer nonwoven materials than the remainder of the topsheet. In addition, all or portions of the tube of absorbent material 22 may also comprise emollients or lubricants for improved comfort and/or easier insertion and removal. Suitable emollients are described in U.S. Pat. No. 5,635,191 entitled "Diaper having A Lotioned Topsheet Containing A Polysiloxane Emollient" issued to Roe, et al. on Jun. 3, 1997, and U.S. Pat. No. 5,643,588 entitled "Diaper Having a Lotioned Topsheet", issued to Roe, et al. on Jul. 1, 1997.

In any of the foregoing embodiments, or other embodiments, the material inside the tube of absorbent material 22 can comprise a blend of more than one type of HIPE foam described in the Absorbent Foam Material patents. Alternatively, the material inside the tube of absorbent material 22 can comprise a blend of the same basic type of HIPE foam, but which has particles with different properties, or a structure comprising portions with different properties.

Figure 12:
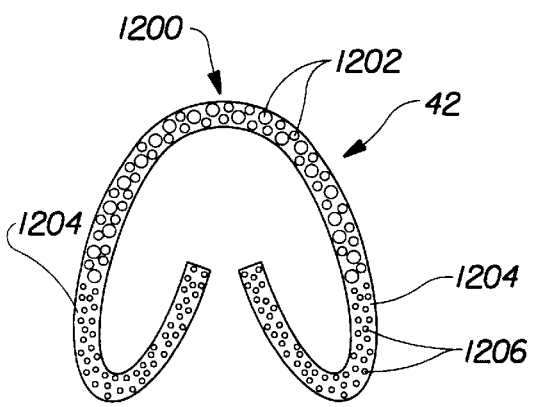
FIG. 12 is a schematic view of an alternative embodiment of the foam absorbent material in its folded configuration, which in this embodiment comprises a sheet that has a central region comprising a soft foam, with large cells and outer regions that comprise a foam that is more firm, and which has smaller cells.

For example, FIG. 12 shows an embodiment in which the absorbent material 42 for the tube of absorbent material 22 comprises a sheet or web of absorbent foam that has been prepared and folded into the desired cross-sectional configuration. The sheet of foam 42 shown in FIG. 12 has a central region 1200 which comprises a soft foam, with large cells 1202 (shown schematically) for improved acquistion, particularly for acquisition of solid material such as cellular debris. The central region 1200 will be in closest contact with the portion of the wearer's body that discharges bodily exudates. The outer regions 1204 of the sheet of foam (that is, the regions that extend toward the longitudinal edges of the same) can comprise a foam that is more firm, and which has smaller cells 1206 to establish a capillary gradient to wick liquids away from the portions 1200 of the foam having the larger cells 1202. The firmer outer regions 1204 may also act to assist in maintaining the central lobe in an upright condition.

In other embodiments, the materials inside the tube of absorbent material 22 may differ from the preferred absorbent foam material described above. For example, the materials inside the tube of absorbent material 22 may comprise a blend of absorbent and non-absorbent foams. Alternatively, thermally bondable materials or other resilient materials may be used in the tube of absorbent material 22. In addition, other types of absorbent materials (e.g., conventional absorbent materials such as wood pulp or other cellulosic fibers, binder fibers, and/or particles or fibers of polymeric gelling agents) can be added to the absorbent material in the tube of absorbent material 22. These types of absorbent materials can be blended homogeneously, or stratified to the central or lower regions of the tube of absorbent material 22.

Figure 13:
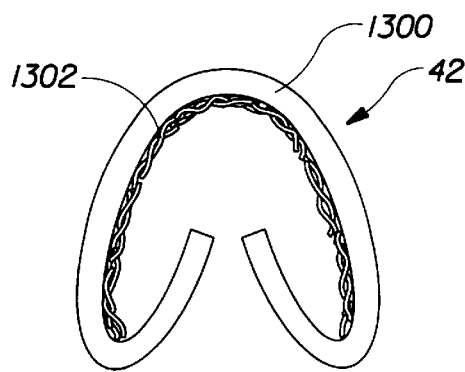
FIG. 13 shows an embodiment in which a foam absorbent material has particles or fibers of polymeric gelling agents in the form of a layer on the underside of a portion of the foam.

For example, FIG. 13 shows an embodiment in which the absorbent material 42 for the tube of absorbent material 22 comprises a folded layer of absorbent foam material 1300. The layer of absorbent foam material has polymeric gelling material in the form of a layer on the underside of at least a portion of the layer of foam 1300. The polymeric gelling agent can be in the form of particles or fibers. In the embodiment shown in FIG. 13, the polymeric gelling material is in the form of fibers of polymeric gelling material in a layer on the underside of a portion of the layer of absorbent foam material 1300.

Figure 14:
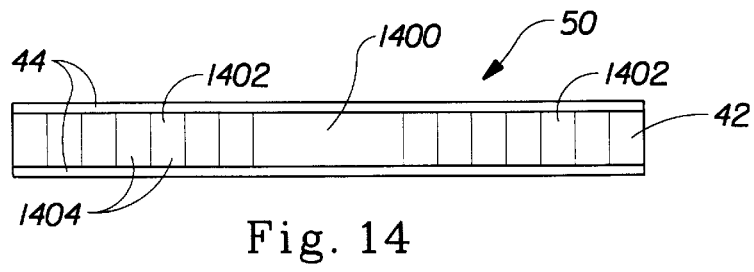
FIG. 14 is a cross-sectional view of a laminate comprising a web of absorbent foam material between a pair of containment webs, in which portions of the absorbent foam material are slit and another portion is left in its original condition.

FIG. 14 shows that in other embodiments, the composite web 50 used to form the tube of absorbent material 22 can be structurally modified to provide regions thereof with different properties. For example, FIG. 14 shows the absorbent foam material 42 that is positioned between two layers of containment web material 44 before folding the composite web 50. The absorbent foam material 42 shown in FIG. 14 has a central region 1400 and side regions 1402 laterally outboard of the central region 1400. The central region 1400 is structurally unmodified (that is, it is left in solid sheet form). The side regions 1402, however, are structurally modified (such as by slitting or forming the same into particles). In either event, absorbent foam material 42 in the side regions 1402 will be divided into (or cut into) separate components. These separate components may be strips or particles and are represented by reference number 1404.

Figure 15:
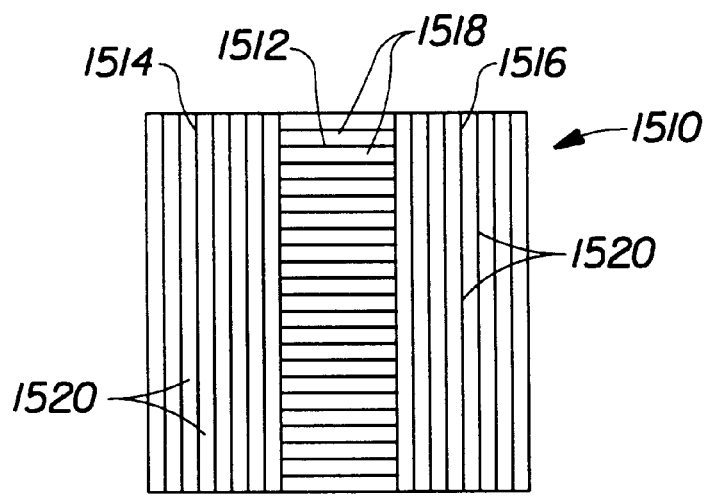
FIG. 15 shows another variation of a web of absorbent material which is provided a longitudinal central region with slits oriented in the transverse direction and longitudinal side regions with slits oriented in the longitudinal direction.

FIG. 15 shows another example of such a structure. FIG. 15 shows a web of absorbent material 1510 that has a region along its longitudinal centerline (a "longitudinal central region") 1512 that has one pattern of slits formed therein, and regions laterally outward therefrom ("longitudinal side regions") 1514 and 1516 that have a different pattern of slits formed therein. Such an absorbent material, which comprises part of a composite absorbent structure, could be folded into a tube-like structure similar to that shown in the preceding figures.

As shown in FIG. 15, the longitudinal central region 1512 can be provided with a plurality of transverse (or cross-machine direction) slits 1518. The transverse slits 1518 can be used to provide the folded tube with greater flexibility along its length than in the transverse direction. The transverse slits 1518 form a plurality of transversely-oriented strips of absorbent material in the longitudinal central region 1512. These strips provide the longitudinal central region 1512 with the ability to preferentially wick (or transport) liquids in the transverse direction. The liquids are preferably transported to the longitudinal side regions 1514 and 1516 to make full use of the web of absorbent material.

The longitudinal side regions 1514 and 1516 are preferably provided with continuous longitudinally-oriented slits 1520 that form a plurality of longitudinally-oriented strips of absorbent material. These strips provide the longitudinal side regions 1514 and 1516 with the ability to transport liquids in the longitudinal direction. The longitudinally-oriented slits 1520 can also be used to avoid any undesirable tendencies for liquids to flow transversely out of the tube of absorbent material by establishing gaps which tend to prevent capillary transport from one strip to the adjacent strip.

Figure 16:
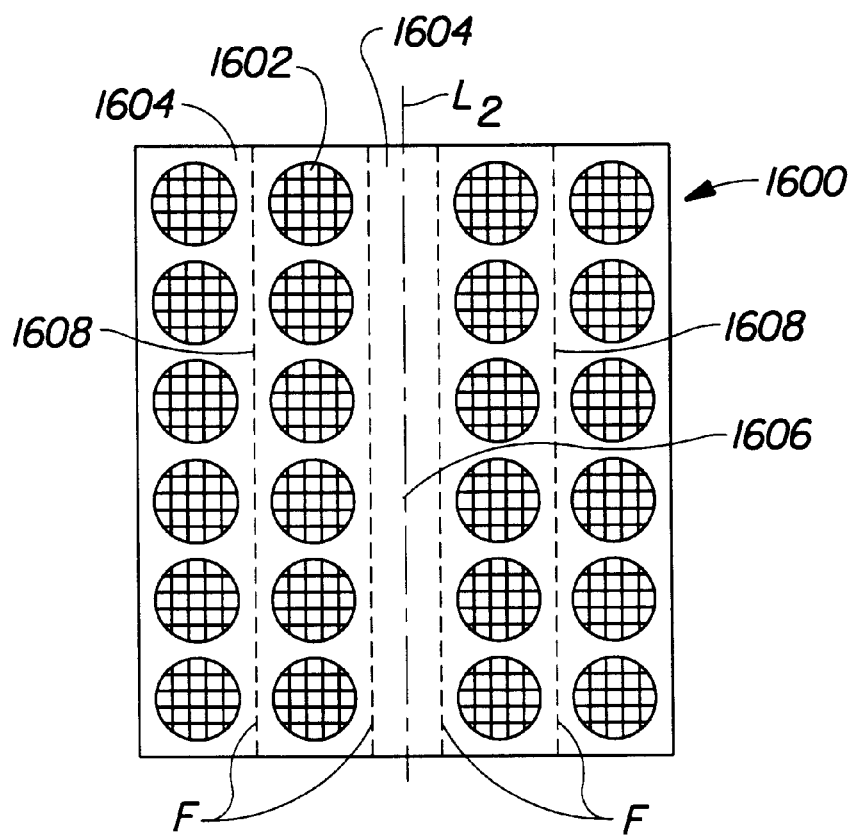
FIG. 16 shows a web of material that has circular portions therein that have been formed into particulate material, and portions that have been unformed, in which the regions are arranged in a pattern so that the unformed portions will form a plurality of spring-like structures when the web is folded.
Figure 17:
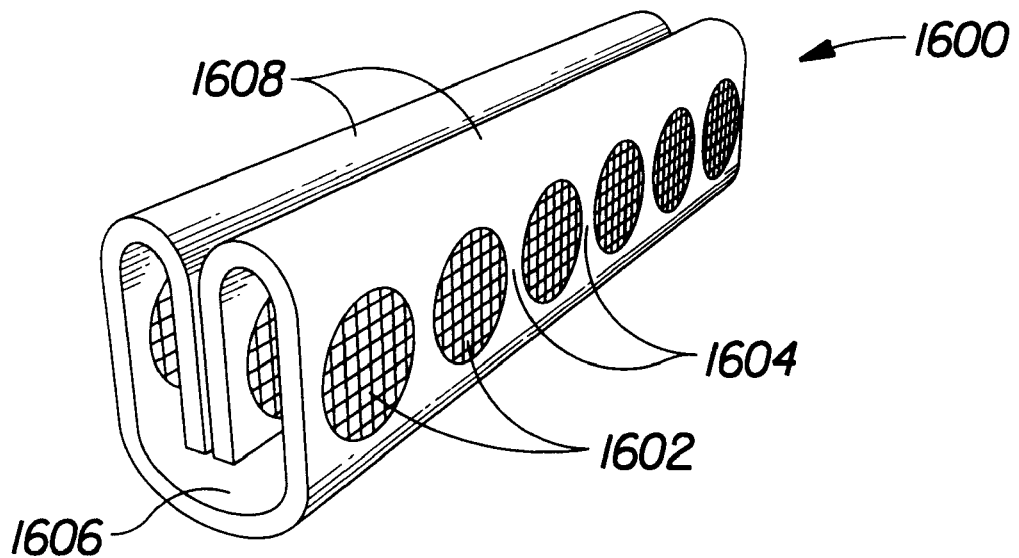
FIG. 17 shows the web of material in FIG. 16 after the same has been folded longitudinally at several places to provide a tube-like structure with spring-like structures on its sides.
Figure 18:
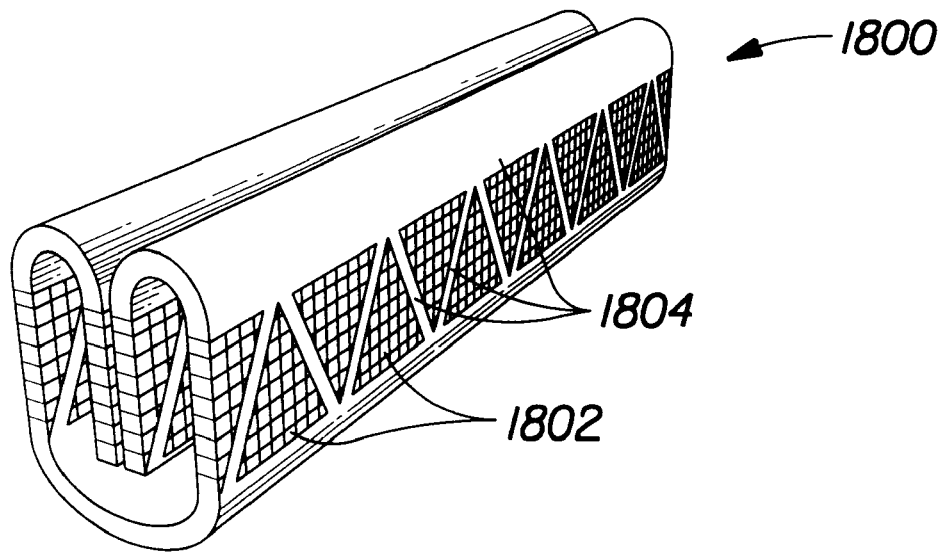
FIG. 18 shows a web of material having particulate portions formed therein which has been folded similarly to the web of material shown in FIG. 17, but the particulate portions are formed in a different configuration to form a truss-like structure.

FIGS. 16 to 18 show still other examples of ways in which the composite web can be structurally modified to provide regions with different properties. These modifications can be used to readily create structures that embody mechanical and/or civil engineering design principles. Such structures include, but are not limited to lattice-like structures, wire frame mesh-like structures, trusses, I-Beam, A-Frame, or lifting springs. Such structures are useful in adding various characteristics, such as: stability, flexibility, and resiliency to the tube of absorbent material 22.

FIG. 16 shows a web of material, such as a web of absorbent material, 1600 that has portions or areas 1602 therein that have been slit or formed into particulate material, and portions 1604 that have been left unformed. The web of material 1600 is shown without the carrier web(s) for simplicity. In the embodiment shown in FIG. 16, an area 1606 along the longitudinal centerline, $L_2$, of the web 1600 is unformed. There are also areas 1608 that lie along prospective folding lines, F, that are unformed. The web 1600 is provided with a plurality of portions 1602 that have been slit or formed into particulate material that are located on both sides of the longitudinal centerline, $L_2$. These portions 1602 are arranged in rows on either side of the prospective folding lines, F. The areas 1602 that have been slit or formed into particulate material are circular in shape. However, in other embodiments, these areas 1602 can be formed in any other suitable shape.

FIG. 17 shows the web of material 1600 shown in FIG. 16 after the web has been folded longitudinally in several places into a tube-like structure. The web 1600 is folded along the longitudinal centerline, $L_2$, and at the folding lines, F, to form the structure shown in FIG. 17. The unformed region 1606 along the longitudinal centerline adds stability to the structure. The circular portions 1602 comprising particulate material along the sides of the structure provide these circular regions with increased compressibility and flexibility. The unformed regions 1604 that surround the circular particulate material portions 1602 provide stability to the sides of the folded structure. The particulate material will remain in place due to the presence of the carrier web. The unformed regions 1604 can act like "springs" when compressive forces are applied to the top or bottom of the folded structure. In variations of the embodiment shown in FIG. 17 (or in any of the other embodiments described herein), the web of material may be provided with slits that run along or across the desired fold lines to provide increased flexibility for ease in folding the web and/or so that the web does not fracture where it is folded.

FIG. 18 shows a tube-like structure formed from a web of material 1800 having triangular-shaped slit or particulate portions 1802 formed therein. The web of material 1800 has been folded similarly to the web of material shown in FIG. 17.

However, in the embodiment shown in FIG. 18, the slit or particulate portions 1802 and the surrounding unformed regions 1804 have different configurations to form a truss-like structure.

In any of the embodiments described herein, the composite web 50 may be folded in different manners to form other three dimensional configurations. Some of these configurations are shown in FIGS. 19 to 23.

Figure 19:
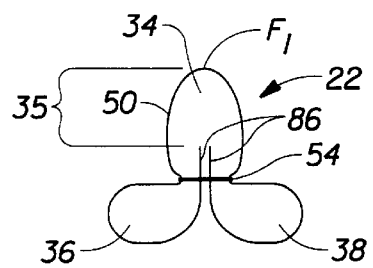
FIG. 19 shows an embodiment in which the composite web is folded so that the longitudinal side margins of the same do not extend as far toward the central fold that forms the central lobe.

FIG. 19 shows an embodiment in which the composite web 50 is folded so that the longitudinal side margins 86 of the composite web 50 do not extend as far toward the central fold, $F_1$, that forms the central lobe 34 as it does in the embodiment shown in FIG. 2. This results in a central lobe 34 which has an upper portion 35 with a reduced transverse width due to fewer layers of material extending into this portion of the central lobe 34. Such an embodiment with a narrower central lobe 34 may be desired by some women for comfort.

Figure 20:
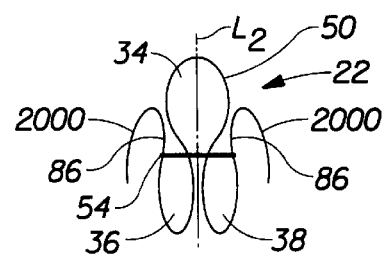
FIG. 20 shows an embodiment in which the composite web is folded in an alternative configuration to provide a pair of flexible side extensions that extend from the central lobe.

FIG. 20 shows an embodiment in which the composite web 50 is folded in an alternative configuration to provide a pair of flexible side extensions 2000. As before, the folded web of absorbent material and the containment web define a central inverted U-shaped cross-sectional configuration which forms the top portion of the folded web (and the central lobe 34). The flexible side extensions 2000 preferably extend laterally outward and downward from the central lobe 34. As shown in FIG. 20, the longitudinal side margins 86 of the composite web 50 are folded outward away from the longitudinal centerline $L_2$ of the composite web 50, rather than inward toward the longitudinal centerline as in the case of the previous embodiments. This fold creates two U-shaped portions along the bottom surface of the folded web of absorbent material, and the longitudinal side margins of the folded web of absorbent material extend upward outside the central inverted U-shaped portion in the direction of the top portion of the folded web. The longitudinal side margins 86 preferably extend upward past the bonded area 54. The longitudinal side margins 86 are then folded back outwardly away from the longitudinal centerline $L_2$ of the composite web 50 so that they extend outwardly and downwardly.

Figure 21:
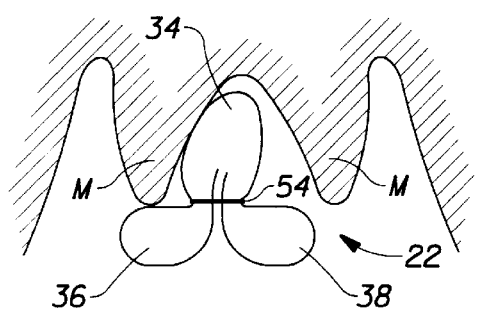
FIG. 21 is a cross-sectional view of a wearer's body surrounding and including the wearer's labia majora and labia minora which shows how a tube of absorbent material might shift to the side when the wearer squats.
Figure 22:
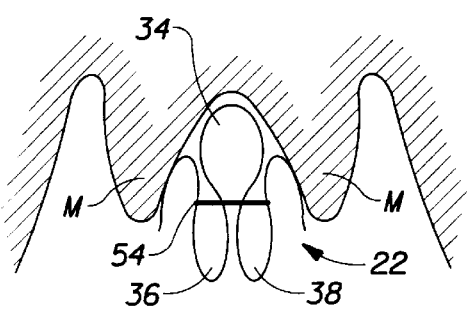
FIG. 22 is a cross-sectional view of the same region of the wearer's body shown in FIG. 21 which shows how a tube of absorbent material with flexible extensions may fit when the wearer squats.

The flexible side extensions 2000 are preferably capable of maintaining contact with and covering the inside surfaces of the wearer's labia when the wearer's body goes through a range of motions, including squatting. The flexible side extensions 2000 also block a direct "line of sight" from the outer perimeter of the labia majora to the vaginal introitus. As a result, body exudates cannot "miss" the tube of absorbent material 22 and the flow of such exudates will be intercepted by the tube of absorbent material 22. The advantage provided by the flexible side extensions 2000 is shown by comparing FIGS. 21 and 22. As shown in FIGS. 21 and 22, when the wearer squats, the labia, M, tend to separate. As shown in FIG. 21, without the flexible side extensions 2000, the central lobe 34 of the tube of absorbent material 22 may tend to adhere to the labia and shift to one side when this happens. The flexible side extensions 2000 are believed to allow the tube of absorbent material 22 to maintain contact with both inside surfaces of the labia as shown in FIG. 22 in order to keep the tube of absorbent material 22 in proper position, rather than adhering to one side of the labia, and shifting to that side.

The flexible side extensions 2000 can be retained in place by exerting a slight laterally outwardly-oriented pressure on the inner surfaces of the wearer's labia minora, labia majora, or both. Additionally, the flexible side extensions 2000 may comprise a material, such as tissue, that will adhere to the naturally moist inside surfaces of the labia. Optionally, the flexible side extensions 2000 may be provided with a bio-compatible adhesive to assist in the adhesion of the flexible extensions 2000 to the inside surfaces of the wearer's labia.

Figure 23:
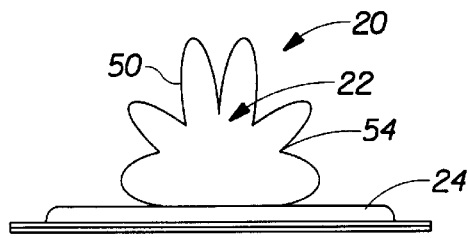
FIG. 23 is a schematic cross-sectional view of an alternative embodiment of the sanitary napkin having a tube of absorbent material that comprises a plurality of lobes.

FIG. 23 shows that in other embodiments, the composite web 50 can be folded multiple times to provide a tube of absorbent material 22 with more than three lobes. Although the tri-lobal cross-section of the tube of absorbent material 22 shown in the preceding figures fits the vast majority of women, in some wearers, due to the shape of the wearer's labia and interlabial space, the central lobe may undesirably be flattened and/or pushed to the side. The embodiment shown in FIG. 23 may be useful in providing a structure that can adapt to fit such wearers' body shapes.

Figure 24:
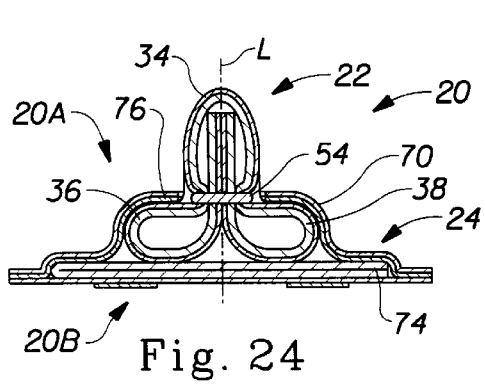
FIG. 24 shows an embodiment in which the tube of absorbent material is integrated into the base pad.
Figure 25:
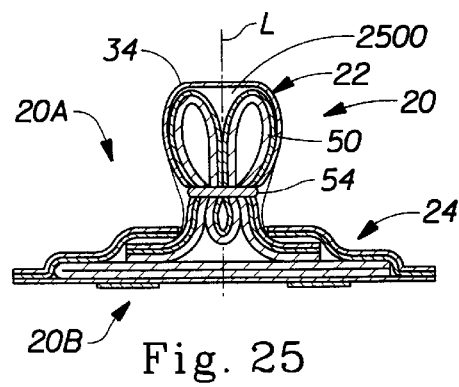
FIG. 25 shows a variation of the embodiment shown in FIG. 24 in which the ocmposite web is folded in an alternative manner so that fewer layers of material are inserted into the base pad.

FIGS. 24 and 25 show alternative ways in which the tube of absorbent material 22 may be joined to the base pad 24.

FIG. 24 shows an embodiment in which the tube of absorbent material 22 is integrated into the base pad 24. In the embodiment shown in FIG. 24, the outer lobes 36 and 38 are positioned between the topsheet 70 (and any optional secondary topsheet 76) and the absorbent core 74. The central lobe 34 extends upward through an opening in the topsheet 70 and the optional secondary topsheet 76 of the base pad 24. The embodiment shown in FIG. 24 provides the advantage of placing the absorbent material in the tube of absorbent material in intimate contact with the absorbent core 74 of the base pad 24.

FIG. 25 shows a variation of the embodiment shown in FIG. 24. In the variation shown in FIG. 25, the composite web 50 that is folded to form the tube of absorbent material 22 is folded in an alternative manner so that fewer layers of material are inserted into the base pad 24. More specifically, the web of absorbent material is folded with the containment web about longitudinally oriented folding axes so that the folded web of absorbent material and the containment web define a pair of central portions which have inverted U-shaped cross-sectional configurations that define an opposed U-shaped cross-sectional configuration therebetween, and the longitudinal side margins of the folded web of absorbent material extend laterally outward at the base of the folded web of absorbent material.

This variation produces a less pronounced change in caliper of the portion of the base pad 24 into which the tube of absorbent material 22 is inserted (or tucked). It also provides the tube of absorbent material 22 with a longitudinally-oriented central groove 2500 which may be useful in the acquisition of cellular debris, and the like contained in blood-based fluids such as menses.

Figure 26:
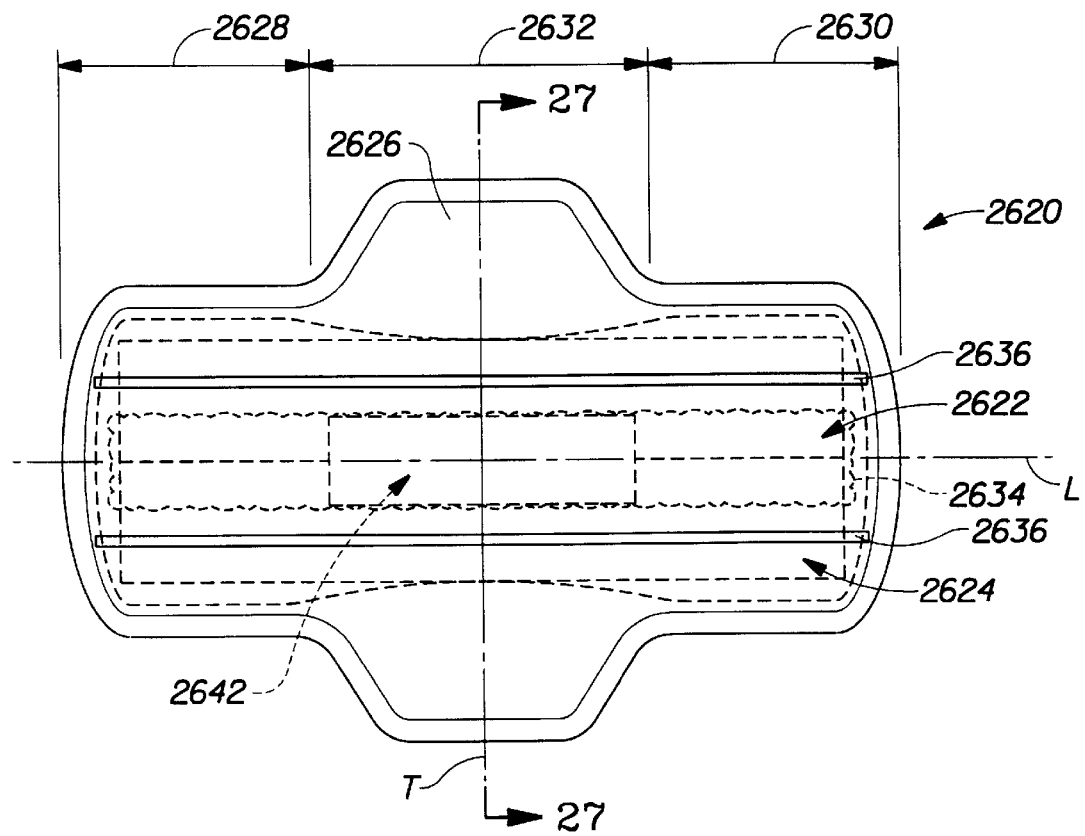
FIG. 26 is a plan view of an alternative embodiment of a compound sanitary napkin in which the absorbent material that is folded to form the tube of absorbent material also forms the absorbent core of the base pad.
Figure 27:
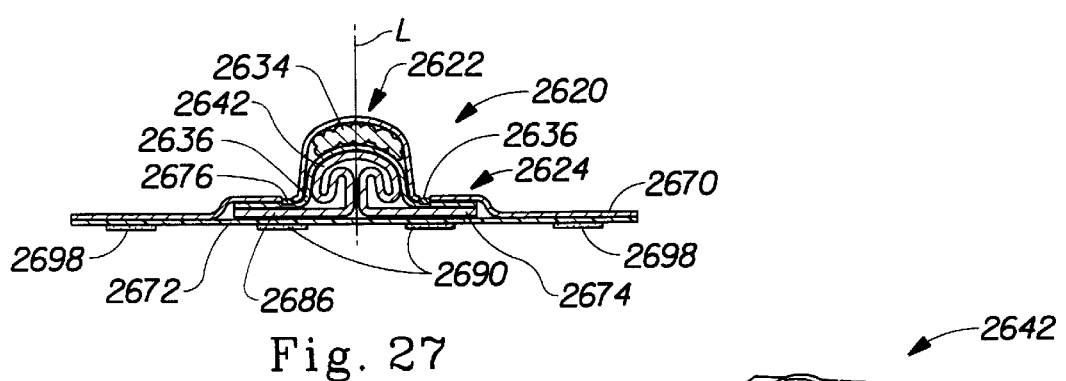
FIG. 27 is a cross-sectional view of the sanitary napkin shown in FIG. 26 taken along line 27—27 of FIG. 26.

FIGS. 26 and 27 show an embodiment of a sanitary napkin 2620 which illustrates still another way in which a tube of absorbent material 2622 may be integrated into the base pad 2624. (The sanitary napkin 2620 shown in FIGS. 26 and 27 also comprises a pair of flaps 2626.) In the embodiment shown in FIGS. 26 and 27, the web of absorbent material 2642 that is folded to form the tube of absorbent material 2622 is positioned underneath the topsheet 2670 of the base pad. The folded web of absorbent material 2642 also forms the absorbent core of the base pad so that a separate absorbent core is not necessary. The absorbent material in the tube of absorbent material and the absorbent core of the base pad can, thus, be described as being "homogenous".

Figure 28:
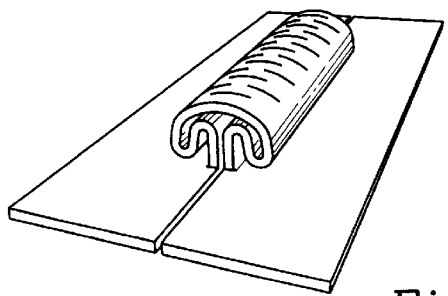
FIG. 28 is a perspective view of the folded absorbent material in the sanitary napkin shown in FIGS. 28 and 27.

The embodiment shown in FIGS. 26 and 27 also shows an alternative manner of forming the tube of absorbent material into a hump which is confined to the central region 2632 of the sanitary napkin 2620. FIG. 28 shows that this embodiment is constructed by cutting the web of absorbent material into an H-shaped configuration before it is folded to form the tube of absorbent material. This produces the structure shown in plan view in FIG. 26, and in cross-section in FIG. 27. The cross-section of the absorbent material 2642 defines a "mini mushroom"-shaped structure. More specifically, the web of absorbent material 2642 has an inverted U-shaped folded portion having a top portion oriented along the longitudinal centerline of the sanitary napkin in a longitudinally-oriented central region of the sanitary napkin which defines the "cap" of the mushroom-shaped structure. The two halves of the web of absorbent material 2642 on either side of the longitudinal centerline are each folded upward inside the inverted U-shaped cap, and then back downward to form the "stem" of the mushroom-shaped structure. The longitudinal side margins 2686 of the folded web of absorbent material 2642 extend laterally outward at the base of the folded web of absorbent material to form the absorbent core 2674 of the base pad 2624.

In this, or any of the other embodiments described herein, the web of absorbent material (such as 2642) can be slitted in the central portion (or any other desired portion) for additional flexibility and/or improved comfort. Suitable patterns for slitting absorbent material are described in U.S. Pat. No. 5,611,790 issued to Osborn, et al.

FIG. 27 shows that in this particular embodiment, the folded absorbent material 2642 is preferably covered by a secondary topsheet 2676. In addition, the top portion of the mushroom-shaped structure has a batt of an acquisition material, such as a high loft material 2634 thereon. The mushroom design concentrates the absorbency in the center of the product. The high loft material 2634 provides rapid acquisition of bodily exudates. The high loft material 2634 may provide quicker acquisition than the absorbent material 2642 to increase the overall acquisition rate of the tube of absorbent material 2622. The high loft material 2634 also provides resiliency and dynamic fit by conforming closely to the configuration of the wearer's body and adjusting to forces placed on it by the wearer's body. The high loft material 2634 can extend any portion of the length of the tube of absorbent material 2622. Preferably, in the embodiment shown, the high loft material extends beyond the ends of the mushroom-shaped structure and substantially the entire length of the sanitary napkin 20. (It should also be understood that such a high loft material can also be used in any of the other embodiments described herein.)

The components of the embodiment of the sanitary napkin shown in FIGS. 26 and 27 can comprise any suitable materials. These materials can include any of those materials specified above as being suitable for the corresponding components of the embodiments shown in the preceding drawing figures. Preferably, in this embodiment, the components of the sanitary napkin 2620 comprise the following materials. The topsheet preferably comprises a DRI-WEAVE apertured film. The high loft material preferably comprises a thermally bonded carded polyester fibrous nonwoven material having a caliper of about 4 mm, a basis weight of about 1.5 oz./yd$^2$ (about 51 grams/m$^2$), and a density of 0.0077 g/cm$^3$, which is obtained as product code #W-4635 from Stearns Technical Textile of Cincinnati, Ohio. The secondary topsheet preferably comprises a 19 g/yd$^2$ (22.5 g/m$^2$) spunbonded polypropylene nonwoven material referred to as product No. 065MLPV60U (or "P-9") obtained from Fiberweb, North America of Washougal, Wash. The web of absorbent material preferably comprises a multi-bonded air laid nonwoven material which comprises about 20% absorbent gelling material, cellulose fibers, powder binder, and latex binder, which has a caliper of about 2 mm, and a basis weight of about 0.077 g/in$^2$ (120 m$^2$). (Unless otherwise stated, all percentages herein are by weight.) Such a multi-bonded air laid nonwoven material is obtained as VIZORB 3900 nonwoven material from Buckeye Canada, Inc., Delta, B. C., Canada. The backsheet 2672 and adhesive fasteners 2690 and 2696 can be any conventional materials used for these components.

The entire assembly of the web of absorbent material 2642, the secondary topsheet 2676, and the batt of high loft material 2634 is preferably covered by the topsheet 2670. Thus, in this embodiment, the web of absorbent material 2642 is wholly integrated into the base pad 2624 to form a longitudinally-oriented absorbent hump. In this particular embodiment, the hump is held in place by fusion bonds 2636 that are preferably located at or slightly outboard of the base of the hump. The fusion bonds 2636 preferably penetrate completely through all of the components of the sanitary napkin 2620. The fusion bonds 2636 can also serve to prevent exudates from wicking laterally outward from the absorbent hump. The fusion bonds 2636 can be in any suitable configuration. As shown in FIG. 26, in this embodiment, the fusion bonds 2636 are preferably in the form of longitudinally-oriented straight lines that extend the length of the sanitary napkin.

Figure 29:
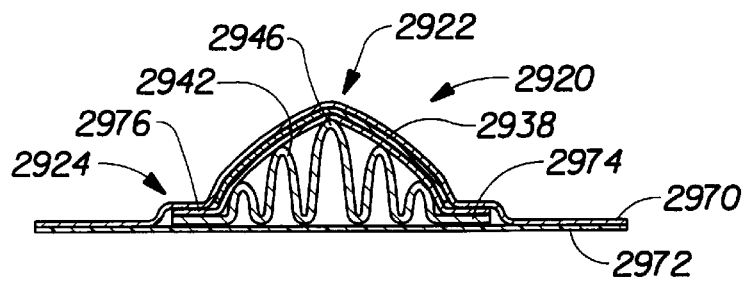
FIG. 29 is a cross-sectional view of another alternative embodiment of a compound sanitary napkin comprising a pleated absorbent material.

FIG. 29 shows another variation of a compound sanitary napkin 2920 in which the absorbent material 2942 is pleated and wholly integrated into the base pad 2924. The absorbent material 2942 shown in FIG. 29 is pleated in a manner that provides a central pleat 2946 that is larger than the pleats located laterally outboard of the central pleat. The pleating provides the sanitary napkin 2920 with the desired hump 2922 configuration. The unpleated longitudinal side margins of the web of absorbent material 2942 extend outward to form the absorbent core 2974 of the base pad 2924. The absorbent material 2942 in this embodiment may, but need not be, cut into an H-shaped configuration before folding in the manner described for the embodiment shown in FIGS. 26 and 27. The sanitary napkin 2920, like the prior embodiments, also comprises a topsheet 2970, backsheet 2972 and an optional secondary topsheet 2976.

The embodiment shown in FIG. 29 can be provided with a number of optimal components and/or features. The embodiment shown in FIG. 29, like any of the other embodiments described herein, can also be provided with a visual indicator, such as a strip of colored material 2938. This colored material 2938 can be used to provide a visual signal to the wearer that the absorbed liquids are primarily retained in the center of the sanitary napkin. This can be used to alleviate the wearer's concerns that the absorbed liquids are traveling toward the longitudinal sides edges of the product, where they might tend to cause soiling of the wearer's undergarments.

In the embodiment shown in FIG. 29, or any of the other embodiments described herein, all or a portion of the topsheet may be mechanically modified for improved softness. For example, it may be desirable to mechanically modify the portion of the topsheet 2970 overlying the hump.

Suitable types of processes for mechanically modifying the topsheet (and/or other components of the sanitary napkin) include, but are not limited to passing the topsheet through a nip between grooved or patterned rolls—a process which has been described as pre-corrugating (or "ring rolling") and forming the components in issue into a structural elastic-like film material (or "SELF" material)—a process that has been referred to as "SELFing" for brevity. Suitable methods for ring rolling are described in U.S. Pat. No. 4,107,364 issued to Sisson on Aug. 5, 1978, U.S. Pat. No. 5,143,679 issued to Gerald M. Weber, et al. on Sep. 1, 1992, U.S. Pat. No. 5,156,793 issued to Kenneth B. Buell, et al. on Oct. 20, 1992, and U.S. Pat. No. 5,167,897 issued to Gerald M. Weber, et al. on Dec. 1, 1992. A method of SELFing a web of material is described in U.S. Pat. No. 5,518,801 issued to Chappell, et al. on May 21, 1996.

Certain types of mechanical modification (ring rolling and SELFing) can also provide the topsheet with the ability to expand to cover the central portion of the tube of absorbent material (for example, the portion comprising the mushroom shaped web in FIGS. 26 and 27) without "blousing" excessively over the portions of the end regions of the tube of absorbent material.

Figure 30:
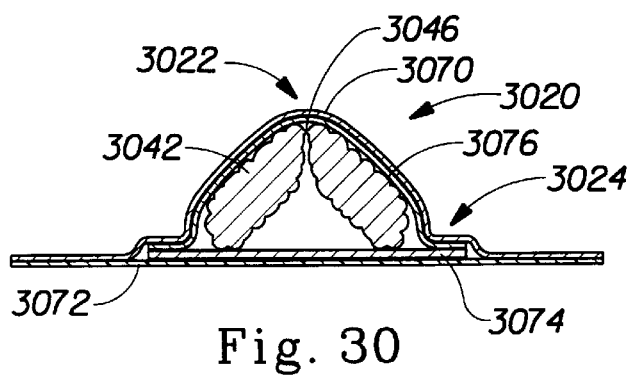
FIG. 30 is a cross-sectional view of another alternative embodiment of a compound sanitary napkin in which the absorbent material inside the tube of absorbent material comprises a higher loft material which is folded into an inverted V-shaped cross-sectional configuration.

FIG. 30 shows still another alternative embodiment of a sanitary napkin 3020. The sanitary napkin 3020 also has a topsheet 3070, a backsheet 3072, and an optional secondary topsheet 3076. The embodiment shown in FIG. 30 has an absorbent web 3042 that is folded in half into an inverted "V-shaped cross-sectional configuration. In cross-section, this folded web 3042 appears to have two "legs" that are connected at the top. The embodiment shown in FIG. 30 can employ a relatively low cost absorbent material that is folded less than the structures described in the preceding embodiments. The embodiment shown in FIG. 30 is intended to provide at least some of the benefits of the structures described above.

The absorbent material 3042 preferably has a greater caliper (e.g., about 10–12 mm) under a confining pressure of 0.1 psi (6.9 kPa)) than the absorbent material used in the foregoing embodiments. It has a longitudinally-oriented compression line 3046 down the center where it is folded. The absorbent material 3042 is compressed to a caliper of about 1–2 mm in the region of the compression line 3046. In addition to assisting the absorbent material 3042 in folding, the compression line 3046 can aid in directing bodily exudates in the longitudinal direction to make use of as much of the capacity of the absorbent material 3042 as possible.

The absorbent material 3042 used in the embodiment shown in FIG. 30 can comprise a number of suitable higher caliper materials. These include, but are not limited to: cotton, thermally bonded air laid nonwoven materials, and multi-bonded air laid nonwoven materials. Preferably, the higher caliper material measures about 8 inch×1 inch (20 cm×2.5 cm), and is capable of retaining 30 g menses under 1 psi (69 kPa) of pressure. One suitable material is an thermally bonded air laid nonwoven material comprising about 20% absorbent gelling material, bi-component fibers, and cellulose fibers. The advantage of using such high caliper materials is that they provide high absorbent capacity in the center of the sanitary napkin. The absorbent capacity may be sufficiently high that a tissue can be used as the absorbent core 3074 of the base pad 3024 to reduce cost. A suitable tissue for use as the absorbent core comprises a piece of BOUNTY paper towel obtained from The Procter & Gamble Company of Cincinnati, Ohio.

Figure 31:
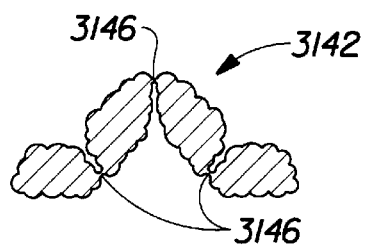
FIG. 31 is a cross-sectional view of another alternative embodiment of a compound sanitary napkin in which the absorbent material inside the tube of absorbent material comprises a higher loft material which is folded into a tri-lobal cross-sectional configuration.

FIG. 31 shows yet another alternative embodiment of a folded higher caliper absorbent web 3142. The absorbent web 3142 shown in FIG. 31 is folded into a tri-lobal configuration. The web of absorbent material 3142 can comprise any of those materials specified above for the preceding embodiment. The embodiment shown in FIG. 31 is formed by forming three longitudinally-oriented compression lines 3146 into the web of absorbent material 3142 and then folding the same into the configuration shown. The compression lines 3146 in the absorbent material 3142 not only assist in folding the absorbent web, but also provide the absorbent material 3142 with the ability to direct the flow of liquid exudates. Liquids will tend to wick toward and along the compression lines 3146 by capillary action. In other embodiments, the pattern of the compression lines can be varied to alter the wicking characteristics.

Figure 32:
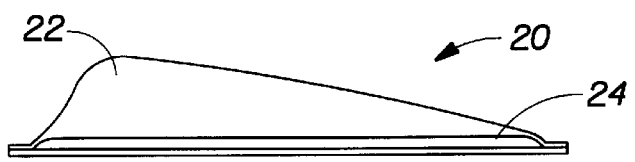
FIG. 32 is a simplified schematic perspective view of a compound sanitary napkin in which the height of the tube of absorbent material varies along the length of the tube of absorbent material.

In any of the embodiments described herein, the height (or caliper) of the tube of absorbent material 22 can vary over any portion of the length thereof. For example, FIG. 32 shows an embodiment in which the height of the tube increases from the front of the sanitary napkin to the rear of the sanitary napkin. This can be used to provide better conformity and contact with the wearer's body in the area of the crevice between the wearer's buttocks (or "gluteal groove"). For example, the web of absorbent material shown in FIG. 31 can have a triangular plan view configuration. When it is folded, the rear of the product will assume the configuration shown in FIG. 31, but the front of the web can be flattened to provide the sanitary napkin with the shape shown in FIG. 32.

FIGS. 33–35 show another way of forming a tube of absorbent material with different calipers along portions of its length. As shown in FIG. 33, to form such a structure, the end regions of a web of absorbent material (or a composite web of absorbent material, or an entire sanitary napkin 3320) may be mechanically stretched (such as by ring rolling or SELFing) to form the web of absorbent material in an hourglass-shaped configuration. The hourglass-shaped web is gathered inward along its longitudinal centerline $L_2$ to form a hump as shown in FIG. 35. The gathered web of sanitary napkin (or sanitary napkin) can be retained in the region of its transverse centerline $T_2$ to form a longitudinally oriented absorbent hump that has a higher caliper in its central region than in its end regions, but is narrower in the central region than in its end regions.

In other embodiments, an hourglass-shaped web of material could be used which is not mechanically stretched. In still other embodiments, the gathering of the web of absorbent material can bring the longitudinal edges of the web inward. The longitudinal edges of the web can be gathered inward in the end regions of the web so that they form straight lines (that is, the web is no longer hourglass shaped). This will result in the portion of the hump formed in the end regions having a greater caliper than the portion of the hump in the central region, and may be modified to have either a greater, lesser, or similar width compared to the portion of the hump in the central region of the sanitary napkin. Preferably, the different portions of the hump taper gradually into one another so that there is a smooth transition therebetween.

A non-limiting number of variations of the embodiment shown in FIGS. 33–35 are also possible. In one variation, the web of absorbent material can be mechanically modified in different manners before it is gathered to form a hump. For example, a web of absorbent material (or an entire absorbent article) can be provided with slits similar to those shown in FIG. 15 before it is gathered to form a hump. The region along all or a portion of the longitudinal centerline of the web of absorbent material can be SELFed in both the longitudinal direction and the transverse direction to form a plurality of particles of absorbent material (as will be described in greater detail below) in this region. The surrounding regions or adjacent regions can be provided with a plurality of longitudinally-oriented slits similar to the web of absorbent material shown in FIG. 15. After gathering, this will result in the portion of the web of absorbent material that forms the hump comprising a plurality of particles of absorbent material, and the surrounding portions comprising plurality of strips of absorbent material. Alternatively, the surrounding regions can be left as a solid piece of material without slitting the same. These embodiments can provide the sanitary napkin with a number of the desired properties, only in a less complicated manner.

FIGS. 36–38 show several possible manners in which the tube of absorbent material 22 particularly a non-integrated (or separate tube of absorbent material) can be joined to the base pad 24. FIG. 4 previously showed an embodiment in which the tube of absorbent material 22 was joined along its entire length to the base pad 24.

FIG. 36 shows an embodiment in which the ends of the tube of absorbent material 22 are joined to the base pad 24, and the portion of the tube of absorbent material 22 between its ends is not joined to the base pad 24. FIG. 37 shows an embodiment in which the tube of absorbent material 22 is permanently joined at one of its ends to the base pad 24, and the other end is releasably attached to the base pad 24. FIG. 38 shows an embodiment in which the tube of absorbent material 22 is releasably attached to the base pad 24 at both of its ends.

The ends of the tube of absorbent material 22 can be releasably attached to the base pad 24 in any suitable manner. In the embodiments shown in FIGS. 37 and 38, the underside of the ends of the tube of absorbent material 22 is provided with an adhesive, such as a pressure sensitive adhesive patch 95. The adhesive patch 95 is releasably joined to an underlying releasable material, such as a release paper 96 of the type conventionally used to cover pressure sensitive adhesives on absorbent articles. Preferably, as shown in FIG. 37, the end 96A (or as shown in FIG. 38, both ends 96A and 96B) of the release paper 96 may be folded over a portion of the body-facing side of the base pad 24 and positioned between the ends of the underside tube of absorbent material 22 and the body-facing side 24A of the base pad 24.

Providing a releasable attachment between one or both ends of the tube of absorbent material 22 provides the ability to allow one end, or both ends of the tube of absorbent material 22 to move freely from the base pad 24, if such freedom of movement is desired for body fit. Providing a releasable attachment at both ends of the tube of absorbent material 22 allows the tube of absorbent material 22 to be removed and re-positioned on the base pad 24 in a location desired by the wearer. This is particularly useful when the tube of absorbent material 22 is not as long as the base pad 24 and the base pad 24 is relatively long and/or asymmetrical about its transverse centerline. In addition, if the tube of absorbent material 22 is soiled, but the base pad 24 is not, providing a releasable attachment at both ends of the tube of absorbent material 22 also allows the tube of absorbent material 22 to be replaced.

Figure 39:
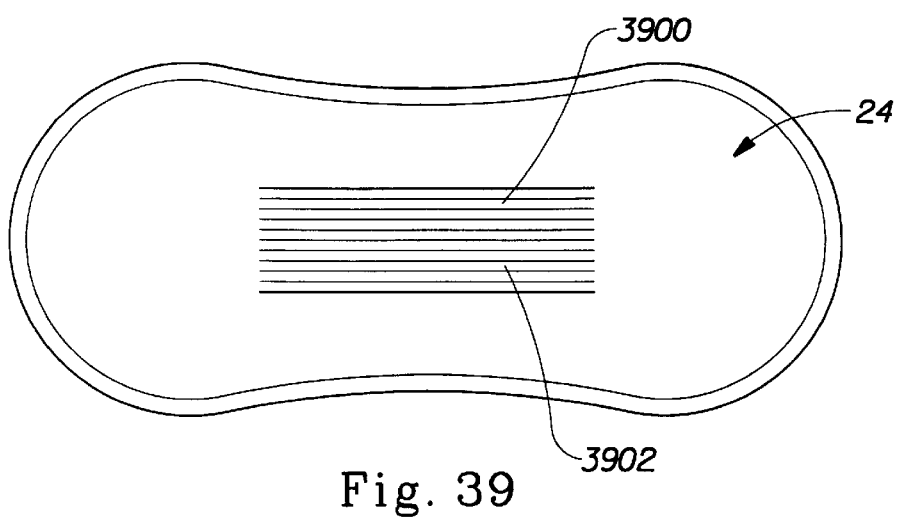
FIG. 39 is a schematic plan view of a sanitary napkin suitable for use as the base pad of a compound sanitary napkin or as a stand-alone sanitary napkin that has a recess therein that can be used by a wearer to insert one or more of her fingers, or portions thereof, in order to assist in the desired placement of the tube of absorbent material or an interlabial portion of the sanitary napkin.
Figure 40:
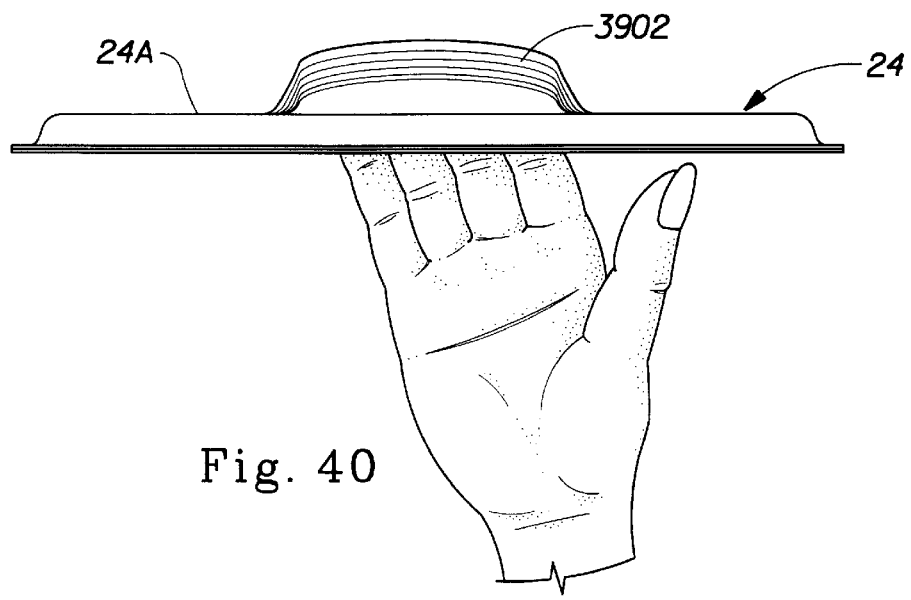
FIG. 40 is a schematic side view of the sanitary napkin shown in FIG. 39 that shows how a wearer can insert one or more of her fingers, or portions thereof, in order to assist in the desired placement of the tube of absorbent material or an interlabial portion of the sanitary napkin.

In any of the embodiments described herein, the base pad 24 may optionally be provided with a displaceable region or area 3900 as shown in FIGS. 39 and 40. The displaceable area 3900 can be used in conjunction with a tube of absorbent material 22 by a wearer to insert one or more of her fingers, or portions thereof, in order to assist in the desired placement of the tube of absorbent material 22. The displaceable area 3900 will typically comprise a recess in the absorbent material, such as a slit or opening in the absorbent material that can accommodate the desired portions of the wearer's fingers or hand. Preferably, the recessed portion of the base pad 24 comprises extensible material 3902 to cover the wearer's fingers when she inserts her hand into the recessed area. Preferably, the extensible material 3902 comprises extensible portions of the topsheet and backsheet. The extensible portions of the topsheet and backsheet are preferably co-planar with the surrounding portions of the topsheet and backsheet until a wearer inserts her fingers into the same. After a wearer inserts her fingers into said displaceable area, said portions of the topsheet and the backsheet can extend beyond the plane of said topsheet and backsheet to move the displaceable area into closer proximity to the space between the wearer's labia.

The extensible material 3902 can comprise any suitable extensible material. In preferred embodiments as shown in FIGS. 39 and 40, the extensible material can comprise portions of the topsheet and backsheet that are rendered extensible by ringrolling or SELFing. These processes may be used to provide these portions of the topsheet and backsheet with extensibility ranging up to as much as 100% to 200%. In addition, if desired, the extensible material 3902 in the recess can also be provided with an absorbent material between the extensible portions of the topsheet and backsheet to provide the pad with a degree of absorbency. In a variation of this embodiment, a base pad 24 (e.g., an ultra thin sanitary napkin) having this feature can be used as a stand alone product without the tube of absorbent material on top thereof.

Figure 41:
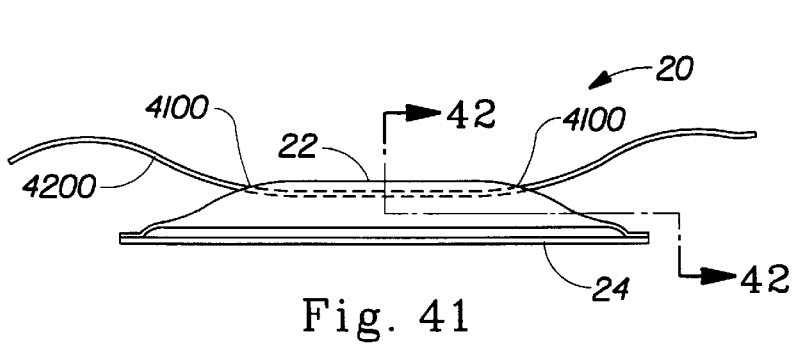
FIG. 41 is a schematic side view of an alternative embodiment of a compound sanitary napkin which has a fit assist mechanism in the form of a removable string that passes through the tube of absorbent material.
Figure 42:
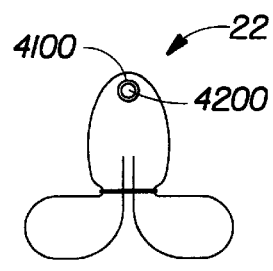
FIG. 42 is a schematic cross-sectional view of the tube of absorbent material of the compound sanitary napkin shown in FIG. 41, taken along line 42—42 of FIG. 41.

FIGS. 41 and 42 show an embodiment of a compound sanitary napkin which has an alternative fit assist mechanism. In the embodiment shown in FIGS. 41 and 42, the fit assist mechanism in form of a removable cinch, such as a string that passes through (e.g. the top of the central lobe of) the tube of absorbent material 22. The wearer can hold both ends of the string to gently pull the tube of absorbent material 22 into the desired interlabially-fitting condition after the compound sanitary napkin is in place in her panties and her panties are pulled up in the usual manner. The string can then be removed when the sanitary napkin is used by pulling the string from one end of the tube of absorbent material 22.

The sanitary napkin 20, in any of the embodiments described herein may also comprise wings or flaps for wrapping around the side edges of the crotch portion of the wearer's undergarment. Typically, such flaps extend laterally outward from at least the central region 32 of the main body portion of the sanitary napkin 20.

Suitable flaps and other types of side wrapping elements are described in Reexamined Pat. No. B1 4,589,876 entitled "Sanitary Napkin", issued to Van Tilburg, Certificate of Reexamination issued Apr. 27, 1993; U.S. Pat. No. 4,687,478 entitled "Shaped Sanitary Napkin With Flaps", which issued to Van Tilburg on Aug. 18, 1987; U.S. Pat. No. 5,281,209 entitled "Absorbent Article Having Tucked Flaps", which issued to Osborn, et al. on Jan. 25, 1994; U.S. Pat. No. 5,389,094 entitled "Absorbent Article Having Flaps and Zones of Differential Extensibility" issued to Lavash, et al. on Feb. 14, 1995; U.S. Pat. No. 5,558,657 entitled "Absorbent Articles Having Overlapping Undergarment Components That Automatically Wrap the Sides of Undergarments", issued to Hammons, et al. on Sep. 24, 1996; International patent application Ser. No. PCT US 96/15957 entitled "Absorbent Article Having Flaps With Step Configuration and Zones of Extensiblity", filed on Oct. 3, 1996, in the name of Lash, et al.; and U.S. Pat. No. 5,669,898 entitled "Absorbent Article With Adjustable Undergarment Protection System" issued to Ahr on Sep. 23, 1997.

2. Method of Making the Sanitary Napkin.

The sanitary napkins described herein can be made by any suitable process.

A. Method of Making the Three Dimensionally-Shaped Tube of Absorbent Material.

FIGS. 43–50 show one preferred process for making the three dimensionally-shaped tube of absorbent material 22 for placement on the body-facing side 24A of a base pad 24 to form the compound sanitary napkin shown in FIGS. 1 and 2. The various embodiments of the sanitary napkin of the present invention are, however, not limited to being made by the process shown in the drawings. It should also be understood that a number of the steps shown in FIGS. 43–50 are optional, but preferred and, thus, are shown since they are useful in making the tube of absorbent material shown in FIGS. 1 and 2.

(1) Assembling The Components.

Figure 43:
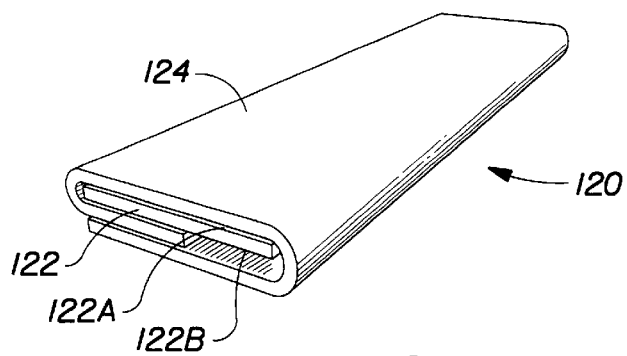
FIG. 43 is a perspective view of a composite web of material that will be shaped into an absorbent tube having a three dimensional shape for use as part of the sanitary napkin shown in FIG. 1.

FIG. 43 shows a composite web of material 120 that will be shaped into the three dimensionally-shaped tube of absorbent material 22 for use in the sanitary napkin shown in FIG. 1. The composite web of material 120 shown in FIG. 43 comprises a first web of material 122 that will form the absorbent material 42 in the tube of absorbent material 22. The first web of material 122 is preferably an absorbent material, such as an absorbent foam material. Preferred absorbent foam materials are those described in the aforementioned Absorbent Foam Material patents.

The preferred absorbent foam materials are generally incompatible with bonding using conventional techniques, such as adhesives, heat and/or pressure, and ultrasonics. The first web of material 122 may, thus, also be referred to as the "web of incompatible material". The web of absorbent foam material 122 has a first bondability (ease of bonding). The web of absorbent foam material 122 may, but need not be, completely incompatible with conventional bonding techniques. Alternatively, it may be a material to which other materials are merely not readily bondable using such techniques. The web of absorbent foam material has a first surface 122A and a second surface 122B. The bondability of the first web of material 122 must be taken into account when assembling the tube of absorbent material, especially when it is necessary to bond the folded composite web 120 in order to retain it in its folded configuration.

The web of absorbent foam material 122 may be not readily bondable to for one or more reasons. Most often, such materials are incompatible with conventional bonding techniques because of their structural integrity or composition. It is difficult to bond other materials to these materials using adhesives because the structural integrity of the such materials is often not as strong as the adhesive bond. As a result, only the portions of the absorbent foam material that are in direct contact with the adhesive will remain bonded to other materials. The remainder of the absorbent foam material will readily separate from the material to which it is bonded. In addition, the foam materials described in the Absorbent Foam Material patents cannot be bonded to other materials using heat bonds because these foams are thermoset polymers. Once they are formed, they cannot be remelted. Instead, when heat is applied to these foam materials, they will char rather than melt and flow, which is needed for heat bonding. These foam materials cannot be pressure bonded to other materials since the thermoset foam materials do not have the ability to flow and be fused under pressure.

The web of absorbent foam material 122 in the embodiment shown in FIG. 43 is at least partially wrapped in a second web of material 124. The second web of material 124 preferably has a second bondability that is higher than the bondability of the web of absorbent foam material 122. That is, the second web of material 124 preferably can be more readily bonded to other materials using conventional bonding techniques. The second web of material 124 may also be referred to herein as a "carrier web" or a "bondable web". The sanitary napkin of the present invention, however, is in no way limited to articles comprising a web of absorbent foam material that is surrounded by a web of material having a higher bondability.

The second web of material 124 is preferably made from a material that is capable of being bonded to other materials, or to itself by heat and/or pressure, or ultrasonics. The second web of material 124 may be manufactured from any of the materials specified above as being suitable for use as the topsheet 40 and/or the containment web 44. The second web of material 124 can be made from a wide range of materials such as woven and nonwoven materials; polymeric materials such as apertured formed thermoplastic films, apertured or unapertured plastic films, and hydroformed thermoplastic films; porous foams, reticulated foams; reticulated thermoplastic films; and thermoplastic scrims.

In other embodiments, the second web of material 124 can be replaced by a material that is in forms other than a web of material. For example, the second web of material 124 may be replaced by a bondable layer or coating such as an extruded glue coating or a silicone coating that is applied to the web of absorbent foam material 122. For this reason, the second web of material 124 may be referred to as the "second material" so that it is clear that materials other than webs are included.

Preferably, the second material 124 comprises a web of material that is also suitable for use as a wrapping for the absorbent material 44 in the tube of absorbent material 22. In the preferred embodiment shown, after processing, the second web of material 124 will serve as the containment web 44 for containing absorbent material in the tube of absorbent material 22. The second web of material 124 preferably comprises a web made of spunbonded nonwoven material. One particularly preferred spunbonded nonwoven material is a 19 g/yd$^2$ (22.5 g /m$^2$) spunbonded polypropylene nonwoven material referred to as product No. 065MLPV60U (or "P-9") obtained from Fiberweb, North America of Washougal, Wash. Another particularly preferred nonwoven material is a spunbonded polyethylene nonwoven material known as COROLIND sold by Corovin GmbH, Peine, Germany, which can be obtained in two basis weights, 23 gsm and 30 gsm.

As shown in FIG. 43, the second web of material 124 is preferably completely wrapped around the web of absorbent foam material 122 so that the second web of material 124 has an "e"-folded configuration in cross-section. Although the second web of material 124 is wrapped around the web of incompatible material 122 in an e-folded configuration, it should be understood that the second web of material 124 is not limited to wrapping the web of incompatible material 122 in an "e"-folded configuration. In other embodiments, the second web of material 124 may only be at least partially folded or wrapped around the web of absorbent foam material 122. The second web of material 124 can be folded or wrapped around the absorbent foam material 122 in any other suitable configurations. Other suitable configurations include, but are not limited to C-folded configurations, and the like.

It is also not necessary that the second web of material 124 be limited to a single web that wraps the web of absorbent foam material 122. One (or more) webs of material may be placed adjacent to each surface 122A and 122B of the web of absorbent foam material 122. For example, in other embodiments, there may be two webs of second material 124, one of which is placed adjacent to each surface 122A and 122B of the web of absorbent foam material 122. In other embodiments, the two webs of material that are placed adjacent to each surface 122A and 122B of the web of absorbent foam material 122 may differ. For example, they may be different types of materials, or they may be the same basic types of materials, but have different characteristics (such as caliper, etc.).

(2) Forming The Absorbent Material Into Particulate Material.

In the preferred embodiment of the process of making the tube of absorbent material 22 shown in the drawings, a single "e"-folded web is used. In an especially preferred version of this embodiment, the web of absorbent foam material 122 will be formed into the particulate material while it is inside the second web of material 124. This will be done by the process described in the commonly-assigned U.S. patent application Ser. Nos. 09/027,039 and 09/027,379 entitled "Method of Making a Slitted or Particulate Absorbent Material and Structures Formed Thereby" and "Method of Making a Slitted or Particulate Absorbent Material" filed in the name of Ronald R. McFall, et al. on Feb. 20, 1998.

In such a case, it is preferable that the second web of material 124, not only be more bondable than the web of absorbent foam material 122, but also that it have a higher yield to break point than the web of absorbent foam material 122. This operation (forming the absorbent foam material into particulate material) is an optional step, but preferable for making the particular embodiment shown in FIGS. 1 and 2. If the absorbent foam material is to remain in sheet form, then this step will be omitted.

The preferred process of forming the absorbent foam material 122 into particulate material shown in the drawings comprises several steps. A "carrier web" having a first yield to break point under tensile forces is provided. (In the embodiment described herein, the second web of material 124 serves as the carrier web.) The web of material for forming into particulate material (which in this case is the web of absorbent foam material 122) and the carrier web are then formed into a composite web 120. The foam absorbent material 122 has a second yield to break point under tensile forces that is lower than the yield to break point of the nonwoven carrier web 124.

The nonwoven carrier web 124 can, if desired, be joined to the web of absorbent foam material. Although the absorbent foam material is incompatible with conventional bonding techniques, if the composite web 120 is not subjected to excessive peel forces, a relatively low level of bonding is sufficient for the purposes described herein. If joined, the nonwoven carrier web 124 is preferably joined to the web of absorbent material by adhesives in an open pattern network of filaments of adhesive as is known in the art.

An apparatus for mechanically straining the composite web 120 is provided. The apparatus preferably comprises a compression device that has at least one component with at least one patterned surface thereon. The composite web 120 is then preferably subjected to a mechanical straining process. In the mechanical straining process, the apparatus impresses a patterned surface into the composite web 120 so that the foam absorbent material 122 is at least partially formed into particulate material without forming the carrier web (second web of material) 124 into particulate material.

Figure 44:
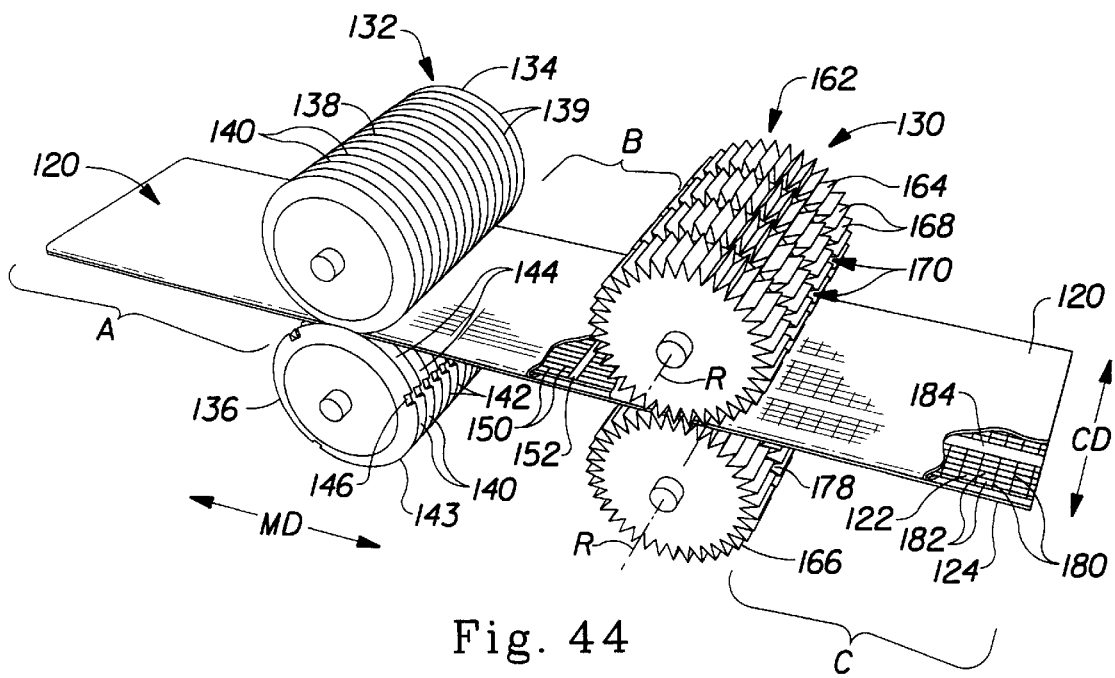
FIG. 44 is a perspective view of an apparatus used to form the absorbent material in the composite web shown in FIG. 43 into particulate material.

FIG. 44 shows one embodiment of an apparatus 130 that is used to form the absorbent material 122 in the composite web 120 into particulate material. The apparatus 130 shown in FIG. 44 comprises two pairs of cylindrical rolls, first pair of rolls 132 and second pair of rolls 162. Each of the rolls has a patterned surface thereon. The patterns are preferably formed by a plurality of ridges and valleys on the rolls that define a plurality of triangularly shaped teeth.

The first pair of rolls 132 comprises a top roll 134 and a bottom roll 136. The rolls 132 and 134 have spaced axes, R. Each of the rolls has a pattern on its surface. In FIG. 44, the top roll 134 has a plurality of ridges 138 and valleys 140 that are disposed around the circumference of the cylindrical roll 134. The ridges 138 form a plurality of triangular-shaped teeth 139 on the surface of the top roll 134 when the top roll 134 is viewed in cross-section. Preferably, the teeth 139 have cross-sections in the form of isosceles triangles. The apex of the teeth 139 may be slightly rounded, if desired.

The teeth 139 on the top roll 134 can be of any suitable size and pitch. The term "pitch", as used herein, refers to the distance between the apexes of adjacent teeth. In the preferred embodiment shown in the drawings, the depth (or height) of the teeth used is preferably between about 0.1 inches and about 0.17 inches (about 2.5 mm to about 4.3 mm ). The pitch is preferably between about 1 mm and about 5 mm, and more preferably is between about 1.5 mm and about 2.5 mm. The pitch of the teeth establishes the width of strips into which the absorbent material is cut or chopped.

The bottom roll 136 in the first pair of rolls shown in FIG. 44 also comprises a plurality of ridges 142 and valleys 144 that are disposed around its circumference. The ridges form a plurality of triangular-shaped teeth 143 on the surface of the bottom roll 136. The teeth 143 on the bottom roll 136 preferably also have cross-sections in the form of isosceles triangles. The teeth 143 on the bottom roll 136 preferably are of the same size as those on the top roll. The bottom roll 136 preferably also comprises several evenly-spaced thin planar channels 146 on the surface of the bottom roll 136 that are oriented parallel to the axis, R, of the bottom roll. In this embodiment, the spaced apart channels 146 in the bottom roll 136 preferably have a width of 2 mm. The "length" of the teeth 143 in the bottom roll 136 measured around the circumference of the bottom roll between the spaced apart channels is 8 mm. A suitable patterned roll for use as the bottom roll is described in U.S. Pat. No. 5,518,801 entitled "Web Materials Exhibiting Elastic-Like Behavior" issued to Chappell, et al. on May 21, 1996.

The triangularly-shaped teeth 139 in the top roll 134 preferably are offset from the teeth 143 on the bottom roll 136. The offset is such that the triangularly-shaped teeth 139 in the top roll 134 align with the valleys 144 on the bottom roll 136. That is, the teeth in the top roll 134 are centered relative to the valleys 144 on the bottom roll 136, and could intermesh (or "engage") the portions of the bottom roll 136 that define the valleys 144 on the bottom roll 136. In this embodiment, however, rolls are preferably spaced so that the triangularly-shaped teeth 139 in the top roll 134 only partially engage with the valleys 144 on the bottom roll 136. The rolls 134 and 136 are preferably driven in opposite directions.

The degree to which the teeth on the opposing rolls intermesh is referred to herein as the "engagement" of the teeth. The engagement of the teeth is the distance between a position where the apexes of the teeth on the respective rolls are in the same plane (0% engagement) to a position where the apexes of the teeth of one roll extend inward toward the valleys on the opposing roll. The engagement of the teeth can be expressed as a percentage of the pitch (distance between the apexes of the teeth on one of the rolls), or in terms of a measured distance. Since the height of the teeth may be greater than the pitch, the engagement may be a value that is greater than 100% (for instance, if the engagement is greater than the pitch). Preferably, the engagement is between about 15% and about 120% of the pitch length, and more preferably is between about 65% and about 100% of the pitch length. The engagement expressed in terms of a measured distance is preferably between about 0.01 inch to about 0.07 inch (about 0.25 mm to about 1.8 mm ), and more preferably is between about 0.04 inch to about 0.06 inch (about 1 mm to about 1.5 mm ).

As shown in FIG. 44, at the stage designated A, the composite web 120 is fed in a machine direction (MD) into the nip between the rolls 134 and 136. The second web of material 124 holds and contains the web of absorbent foam material 122 which is about to be slit and formed into particulate material. The second web of material 124 wraps the outside of the web of absorbent foam material 122 so that the second web of material 124 faces the patterned surfaces on the rolls 134 and 136.

The rolls 134 and 136 subject the composite web 120 to a mechanical straining process by impressing the patterned surfaces into the composite web 120. The mechanical straining process applies a force that is greater than the yield to break point of the web of foam absorbent material 122, but less than the yield to break point of the nonwoven carrier web 124 so that the web of foam absorbent material 122 is at least partially slit without slitting the carrier web 124.

FIG. 44 shows the condition of the composite web at stage B, after it passes through the nip between the first pair of rolls 132. As shown in FIG. 44, the carrier web 124 will have a pattern formed therein that corresponds to the combination of the patterns on the adjacent rolls, 134 and 136. The carrier web 124, however, is not slit or cut. The intermediate web of absorbent foam material 122 has a plurality of slits 150 formed therein. The slits 150 are oriented in the machine direction (or "MD"). In the particular embodiment shown, the slits are intermittent and separated by cross-machine direction (or "CD") bands of unslit material 152. This is due to the presence of the channels 146 on the bottom roll 136. The web of absorbent foam material 122 is slit while the carrier web 124 is not slit because the web of foam absorbent material 122 has a lower yield to break point than the carrier web 124, and breaks, under tensile forces (the straining process) while the carrier web does not.

The web of absorbent material 122 need not have bands of unslit material 152 therein. In other embodiments, continuous slits can be formed in the web of absorbent material 122. Continuous slits 150 will be formed if the bottom roll 136 is modified by replacing the channels 146 therein with sections that form continuous ridges and valleys. In such an embodiment, the bottom roll 136 will be identical to the top roll 134. If the slits 150 are continuous, the web of absorbent material 122 will be formed into a plurality of strips 151 that have been separated by the slitting process. These may be referred to as "strands" herein, although they are not comprised of wound fibers or the like. These strips or strands 151 can be very narrow, or they can be fairly wide with widths increasing up to slightly less than the width of the web (depending on the apparatus used).

If these strips 151 are very narrow, they may resemble spaghetti noodles in the overall dimensions. However, the sides of these strips would typically be flat, rather than rounded. The width of the strips 151 depends on the pitch of the teeth on the rolls. Thus, some non-limiting dimensions of the strips 151 in the preferred embodiment shown might range from about 1 mm to about 5 mm wide, and are preferably between about 1.5 mm and about 2.5 mm wide. The strips 151 can be any suitable length. They can range from lengths that are slightly greater than their width dimension, to an infinite length. Typically, their maximum length will be limited by the length of the product into which they are incorporated.

Figure 48:
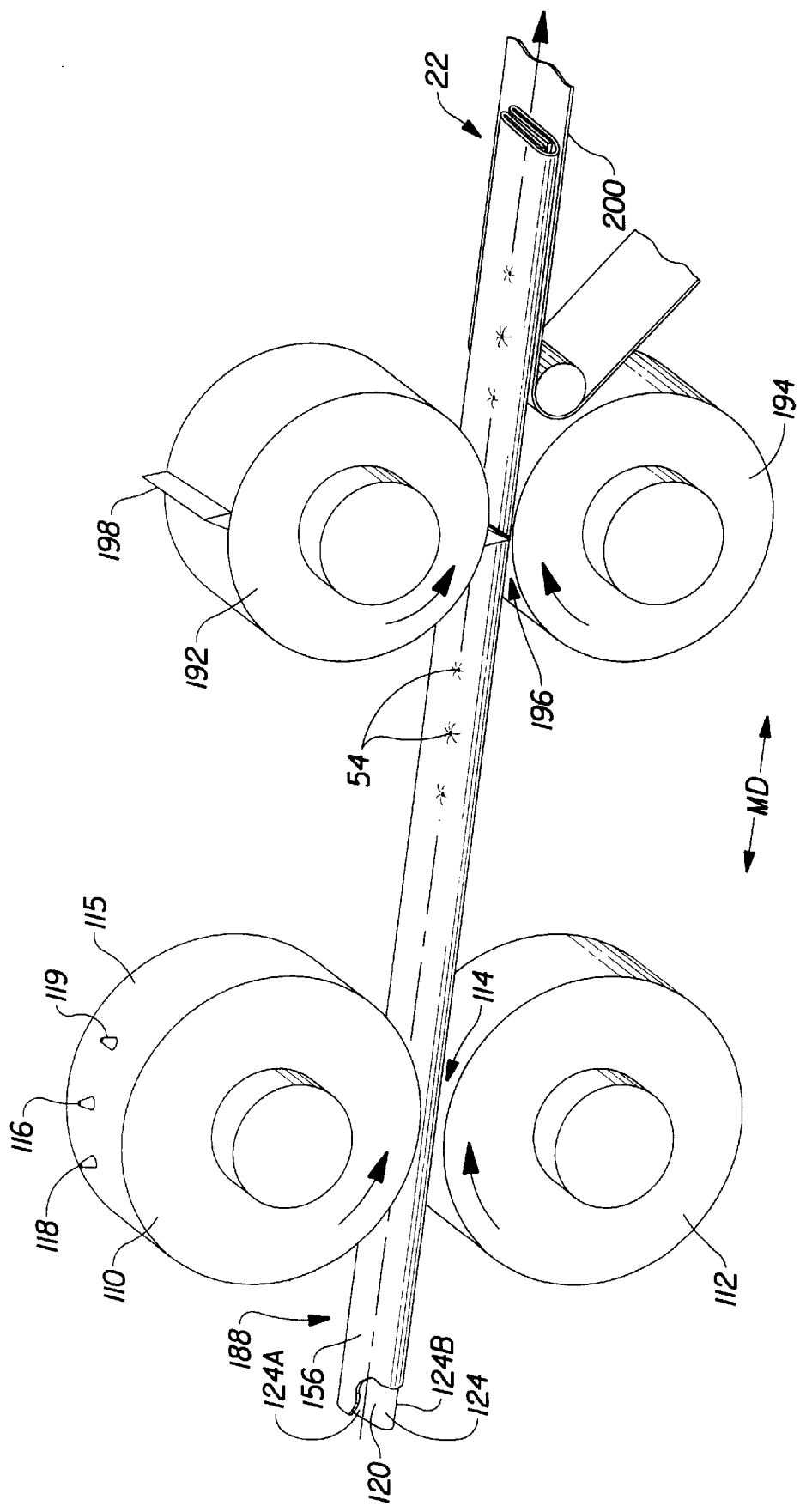
FIG. 48 is a perspective view of one embodiment of the method of the present invention which is used to make a make a tube of absorbent material.

At this point in the process, (at stage B, between the first and second sets of rolls, 132 and 162) it is possible to perform additional operations on the composite web 120. For example, the composite web 120 can be cut into discrete lengths between the first and second sets of rolls 132 and 162. In other embodiments, the composite web 120 can be cut into discrete lengths by a cutting blade located on one of the rolls in the first set of rolls 132. In still other embodiments, as shown in FIG. 48, the composite web 120 can be cut into discrete lengths by a cutting blade located on an apparatus that the composite web passes through subsequent to the second set of rolls 162. The lengths correspond to the size of the tube desired for the sanitary napkin shown in FIG. 1. The cutting of the composite web 120 has been omitted from FIG. 44 for simplicity of illustration.

Figure 45:
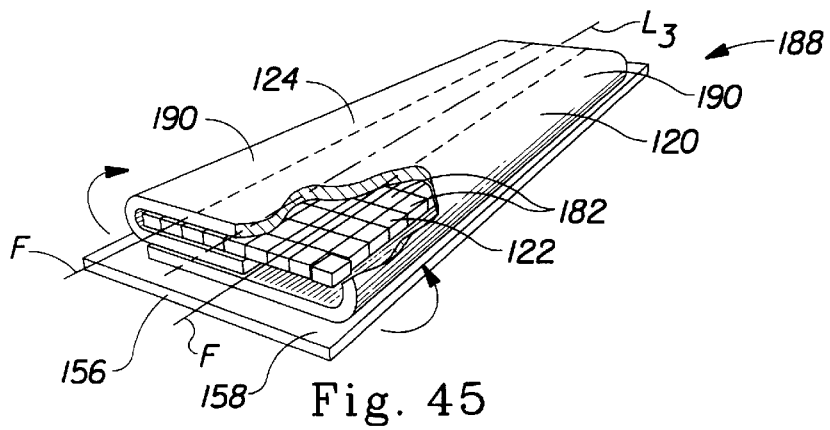
FIG. 45 is a partially fragmented perspective view of the composite web shown in FIG. 43 after it has been fed through the apparatus shown in FIG. 44.

Further, an additional web of material, such as a sheet of apertured film topsheet material 156, can be joined to the composite web 120. Such a sheet of topsheet material will become the topsheet 40 on the sanitary napkin shown in FIGS. 1 and 2. The additional web of material can be joined to the composite web 120 at any suitable place in the process. For example, the additional web can be joined to the composite web 120 before or at the first set of rolls 132, between the first and second sets of rolls, or at or after the second set of rolls 162. The topsheet material can be in the form of a continuous web, or in the form of individual pieces that correspond to the size of the tube desired for the sanitary napkin shown in FIG. 1. The joinder of the apertured film topsheet material 156 to the composite web 120 is shown in FIG. 45. It has also been omitted from FIG. 44 for simplicity of illustration. The apertured film topsheet material 156 is preferably joined to the composite web 120 by adhesives. This forms a structure that will be referred to herein as "tube forming composite web"188.

The second set of rolls 162 of the apparatus 130 for mechanically straining the composite web is shown in FIG. 44. The second set of rolls 162 also comprises top and bottom rolls, 164 and 166, respectively. Each of these rolls also has a pattern on its surface. As shown in FIG. 44, the top roll 164 has ridges that run parallel to the axis of the top roll 164 that are oriented so that they define triangular-shaped teeth 168. The top roll 164 may also have a plurality of spaced apart channels 170 that are oriented around the circumference of the cylindrical roll. The bottom roll 166 of the apparatus shown in FIG. 44 is similar to the top roll 164. Suitable patterned rolls for use as the rolls in the second pair of rolls 162 (though not for this purpose) are described in greater detail in U.S. Pat. No. 5,518,801 entitled "Web Materials Exhibiting Elastic-Like Behavior" issued to Chappell, et al. on May 21, 1996.

In the preferred embodiment shown in the drawings, the top and bottom rolls 164 and 166 in the second set of rolls 162 have teeth and ridges and valleys having similar characteristics to those elements of the first set of rolls. Thus, the teeth are preferably in the shape of isosceles triangles. The teeth preferably also have the same pitch. However, in other embodiments, the pitch of the teeth on the second set of rolls 162 can be less or greater than the pitch of the teeth on the first set of rolls 132. In the preferred embodiment shown, the spaced apart channels 170 and 178 in the second set of rolls preferably have a width of 2 mm. The "length" of the teeth measured transversely across the rolls (parallel to the axes, R) between the spaced apart channels 170 and 178 on the surface of each roll is 8 mm. The triangular-shaped teeth on the top and bottom rolls preferably also have the same engagement as the teeth on the first set of rolls, although the engagement can be varied as well. The top and bottom rolls are preferably rotating in opposite directions. The composite web 26 is similarly fed into the nip between the rolls 164 and 166.

FIG. 44 shows that when the composite web 120 leaves the nip between the second set of rolls 162, at least a portion of the absorbent foam material 122 is further provided with a plurality of slits 180 that are oriented in the cross-machine direction. This initial slitting in the machine direction and subsequent slitting in the cross machine direction results in the absorbent material 122 being formed or chopped into a plurality of particles 182. In the preferred embodiment shown in the drawings, the particles 182 have a square surface area that is about 1.5 mm×1.5 mm. The particles 182 are preferably about 2 mm thick (the thickness of the absorbent foam material). The absorbent material 182 can optionally have unslit strips 184 left therein due to the presence of the channels 170 in the second pair of rolls 162.

Again, the nonwoven carrier web 124 is not slit, but has another pattern formed therein. The overall pattern formed therein resembles a grid with a combination of the impressions created by the first and second sets of rolls 132 and 162. The apertured film topsheet 156, if fed into the process between the first and second set of rolls, will have a pattern formed therein that resembles that of the second set of rolls 162.

FIG. 45 shows the composite web 120 after it has been fed through the apparatus shown in FIG. 44. As discussed above, a sheet of apertured film topsheet material 156 has preferably been joined to the composite web 120. FIG. 45 shows that the sheet of apertured film topsheet material 156 is preferably of a size that is about the same width as, but longer than, the individual lengths that the composite web 120 was cut into. The apertured film 156 extends beyond the ends of the individual lengths of composite web material so that the tube of absorbent material, once formed, can be more easily attached to the sanitary napkin, when the ends of the same are fused to the base pad of the sanitary napkin.

It should be understood that in FIG. 45, the pattern impressed into the nonwoven material 124 by the first and second sets of rolls has been omitted or simplicity. In addition, the foam absorbent material 122 is shown as comprising only particles 182 for simplicity (that is, no unslit strips are shown as being left in the incompatible material 122). Such an embodiment could be created by providing the rolls on the first and second sets of rolls 162 with continuous teeth and omitting the channels 146, 170, and 178 between the teeth.

It should be also understood that the drawings illustrate a particularly preferred manner of forming the absorbent foam material into particles. The method of making the sanitary napkin of the present invention is not limited to a process which involves forming the absorbent foam material into particles in the manner shown in the drawings.

(3) Folding the Tube Forming Composite Web.

Figure 46:
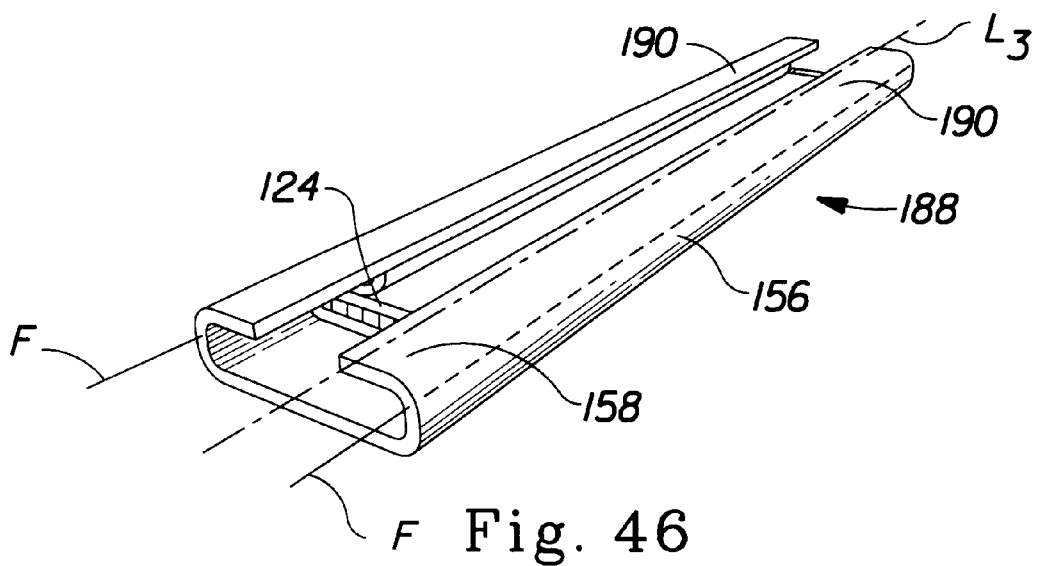
FIG. 46 is a perspective view of the composite web shown in FIG. 43 after the side margins have been folded in a first folding operation.

The next step in making the tube of absorbent material for the sanitary napkin shown in FIG. 1, is folding the combination of the composite web 120 and the sheet of apertured film topsheet material 156 (the tube forming composite web) 188. FIG. 45 shows the longitudinally-oriented folding lines, F, about which the longitudinal side margins 190 of the tube forming composite web 188 will initially be folded. FIG. 46 shows the tube forming composite web 188 after the side margins 190 thereof have been folded along folding lines F in a first folding operation to form a "C"-folded structure.

Figure 47:
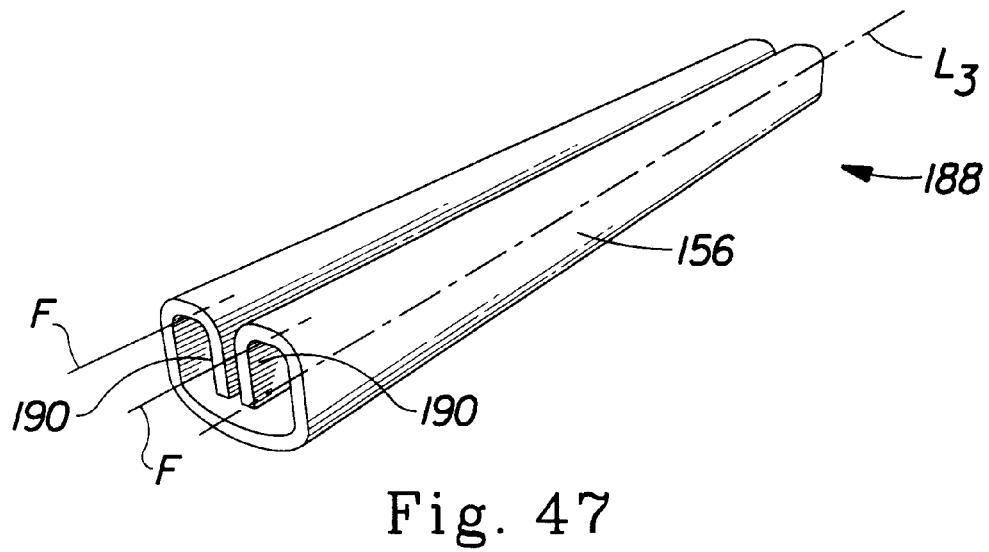
FIG. 47 is a simplified schematic perspective view of the composite web shown in FIG. 43 after it has been folded in a second folding operation.

FIG. 47 shows the tube forming composite web 188 after it has been folded in a second folding operation. As shown in FIG. 47, the tube forming composite web 188 has been folded along its longitudinal centerline, $L_3$. As a result, the previously-folded longitudinal side margins 190 are brought adjacent to each other, and the longitudinal side margins 190 of the tube forming composite web 188 are tucked inside the folded tube forming composite web 188. As shown in FIG. 47, the folded longitudinal side margins 190 lie adjacent to the longitudinal centerline, $L_3$, of the tube forming composite web 188. The folded tube forming composite web 88 shown in FIG. 47 is now ready to be bonded and shaped into the desired three dimensionally-shaped structure.

(4) Bonding and Shaping the Tube Forming Composite Web.

In the process shown in the drawings, in order to bond and shape the absorbent foam material, in the most general sense, at least portions of the web of material having the higher second bondability (the nonwoven) 124 positioned to the outside of the absorbent foam material 122 (the incompatible material). The cross-section of the actual structure being bonded (as shown in FIG. 50) is somewhat more complicated than that, but for the purposes of the present description, the above-described general relationship (with the web of material having the higher second bondability positioned outside of the web of absorbent foam material) is preferably present.

The folded tube forming composite web 188 is then bonded with one or more bonds 54. The bonds 54 penetrate the incompatible absorbent foam material 122, and join one portion of the nonwoven web 124 to another portion of the nonwoven web 124 on the opposite side of the absorbent foam material 122. The number of bonds 54 and placement of the bonds depends on the configuration desired for the tube of absorbent material 22. For making the particular tube of absorbent material shown in FIGS. 1 and 2, two to five bonds 54 are preferably used. In the embodiment shown in the drawings (see FIG. 49), three bonds 54 are used. The bonds 54 are preferably spaced about 1.75 inches (about 4.4 cm) apart, and are located about 17 mm from the fold made along the longitudinal centerline, $L_3$, of the tube forming composite web 188. While the sanitary napkin of the present invention and the method of making the same can utilize bonds of any suitable size, bond sizes that have been found to be suitable have a circular plan view configuration with a diameter of about 3 mm and an area of about 8 mm$^2$.

The bonding can be accomplished using heat and/or pressure, or by ultrasonics. Suitable techniques for heat and/or pressure bonding are described in greater detail below. Suitable techniques for ultrasonically bonding are described in Procter & Gamble U.S. Pat. No. 4,430,148 entitled "Ultrasonic Bonding Process" issued to Schaefer on Feb. 7, 1984, and U.S. Pat. No. 4,823,783 entitled "Adhesive-Free Bonding of Continuously Moving Webs to Form Laminate Web and Products Cut Therefrom" issued to Willhite, Jr., et al. on Apr. 25, 1989.

FIG. 48 shows one preferred embodiment in which the bonding is accomplished by dynamically bonding portions of the second web of material (nonwoven covering) 124 and/or the apertured film topsheet material 156 on each side of the absorbent material 122 together using pressure and optionally, heat. Many of the principles described for this process are similar to those which would apply if ultrasonics are used. In the embodiment shown, at least one of the materials to be bonded (the nonwoven covering or the apertured film topsheet material) preferably comprises thermoplastic material. (It should be understood that, for simplicity, the bonding will be expressed below in terms of bonding portions of the nonwoven covering 124 together, even though portions of the apertured film topsheet material may be similarly bonded in the process.)

As shown in FIG. 48, a first portion 124A of the cover material 124 is preferably bonded through the tube forming composite web 188 to a second portion 124B of the cover material. The apparatus used for bonding the tube forming composite web 188 preferably comprises a pair of cylindrical rolls 110 and 112. Preferably, at least one of the rolls, roll 110, has a relief pattern on its surface. The patterned roll 110 is configured to have a circular cylindrical surface 115, and a plurality of protruberances or pattern elements (or "pattern element segments") 116 which extend outwardly from the surface 115.

The relief pattern can be in any suitable configuration. It can be linear, curvilinear, or it can be comprised of linear segments and curvilinear segments. The relief pattern can be continuous or intermittent. The relief pattern can define an unlimited number of patterns and other types of designs. For example, it can define geometric shapes, arrows, words, etc. The land surfaces 118 on the pattern element segments can also be provided in a wide variety of possible shapes. Suitable shapes for the land surfaces 118 include, but are not limited to, oval and circular.

The relief pattern, in the embodiment of the apparatus shown, comprises a plurality of spaced apart pattern elements 116 having circular land surfaces 118. In the embodiment of the method shown in FIG. 48, the pattern elements 118 are arranged in an intermittent linear configuration.

The pattern elements 116 preferably have side walls 119 that are not perpendicular with the surface of the cylindrical roll. Preferably, the side walls 119 of the pattern elements 116 form an angle of between about 60–70 degrees with surface of the cylindrical roll. Modifying the orientation of the side walls of the pattern elements 116 is necessary due to the thickness of the absorbent material between the materials being bonded, and the desire to avoid tearing the cover material 124.

The other roll 112, serves as an anvil member and, thus, may be referred to as anvil roll 112. The patterned roll 110 and the anvil roll 112 define a pressure biased nip 114 therebetween. Preferably, the anvil roll 112 is smooth surfaced. In other embodiments, however, both rolls 110 and 112 may have a relief pattern and/or pattern elements thereon. If that is the case, the pattern elements on opposing rolls will preferably be aligned with each other to compress the materials to be bonded therebetween.

The patterned roll 110 and anvil roll 112 are preferably biased toward each other with a pre-determined pattern element loading of from about 20,000 psi (about 140 Mpa) to about 200,000 psi (about 1,400 MPa).

The patterned roll 110 and the anvil roll 112 are preferably driven in the same direction at different speeds so that there is a surface velocity differential therebetween. The surface velocity differential preferably has a magnitude of from about 2 to about 40 percent of the roll having the lower surface velocity, more preferably between about 2 to about 20 percent. The anvil roll is preferably operated at a surface velocity that is greater than the surface velocity of the patterned roll 110. A method of dynamically bonding a laminate between a pair of rolls having a surface velocity differential therebetween is described in greater detail in U.S. Pat. No. 4,854,984 issued to Ball, et al on Aug. 8, 1989.

The method may further comprise the step of heating one or both of the rolls. If the rolls are heated, they are preferably heated to a surface temperature that is a predetermined number of degrees below the melt temperature of the thermoplastic material in the cover material 124. It is also possible, at high line velocities, for the bonding to occur at zero velocity differential (that is, with the nip defining rolls having equal surface velocities).

The bonding process shown in the drawings penetrates through the tube forming composite web 188 and autogenously bonds the first portion 124A of the nonwoven cover material to the second portion 124B of the cover material 124. The term "autogenous", as used herein, refers to bonding without a third material such as stitching or adhesives. The method described herein, however, is not intended to be limited to one which precludes stitching or adhesive augmentation of such autogenous bonding.

FIG. 50 shows that the bonding compresses, or more preferably, displaces the foam absorbent material in localized areas where the bonds 54 are formed. This isolates a three-dimensionally shaped portion 100 of the web of particles of foam material from the remainder of the web of particles of foam absorbent material (referred to generally by reference number 102) and forms the isolated portion 100 (as well as the entire tube forming composite web 188) into a distinct shape.

Figure 49:
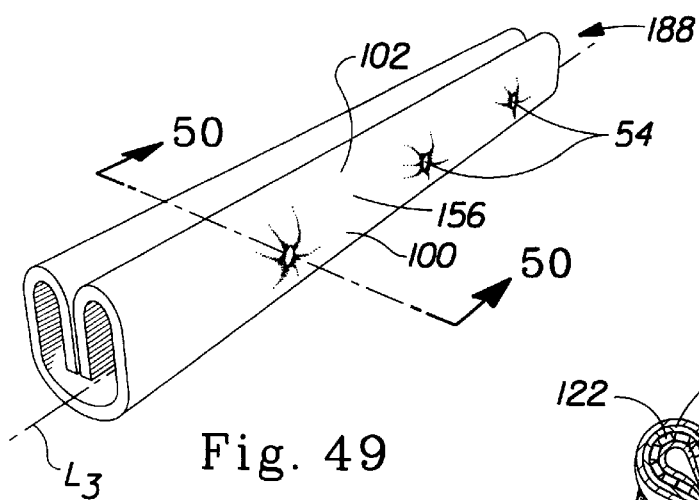
FIG. 49 is a simplified schematic perspective view of the composite web shown in FIG. 28 after it has been shaped by bonding portions thereof together.

In the embodiment shown in the drawings, the bonding forms the tube forming composite web 188 into a profiled shape in which the portion of the composite web 188 that will form the top of the absorbent tube on the finished product, is given a narrower width. Preferably, as shown in FIG. 1, the portion of the composite web 188 that will form the top of the absorbent tube on the finished product defines a ridge 60 that projects perpendicularly from the top of the remainder of the absorbent tube (and the remainder of the sanitary napkin). As shown in FIGS. 1, 49 and 50, the bonding also provides the composite web 188 with tufted regions 56 where the tube forming composite web 188 is puckered around the bond sites 54.

The bonds 54 can be placed in a virtually unlimited number of patterns to create products having a virtually unlimited number of possible geometric shapes. The bonding patterns can also be used to add structural stability as well as shaping the tube of absorbent material by adding a degree of stiffness to the product along a line that passes through the bonds. This line can be rectilinear, curvilinear, or partially rectilinear and partially curvilinear. The method of bonding described herein can also be used on a manufacturing line running at high speeds (e.g. 700–1,000 feet per minute), and is not limited to particular patterns, as are sewing processes. (Of course, in less preferred embodiments sewing or other processes can be used to maintain the tube of absorbent material in the desired cross-sectional configuration.)

FIG. 50 also shows that the bonds 54 penetrate the layer of particles of foam material 122. The bonds 54 are formed between the opposed portions of the nonwoven web of material 124 having the higher second bondability that are positioned outside the particles of foam material 122. The bonding mechanism preferably slices through or displaces the particles of foam material 122 so that there is a clear path for the bondable materials to bond together. Preferably, very little (if any) of the foam material is actually left in the bond sites.

Another advantage of slitting or forming the absorbent material into particulate material, especially where the slit or particulate material is adhered to a carrier web, is that the method used to form the slit or particulate material may be used to provide a continuous clear path for the bonds to penetrate through the absorbent material. Methods of chopping absorbent material which merely chop the absorbent material and blow it into a closed tube by air will result in a random distribution of the chopped particles. Such methods are less preferred because they will not form the clear path for bonding described herein.

After the bonding process, the bonded tube forming composite web 188 is preferably cut to form a plurality of individual tubes of absorbent material 22.

The apparatus used for cutting the bonded tube-forming composite web 188 is also shown in FIG. 48. The apparatus comprises a pair of rolls 192 and 194. One of the rolls, roll 192, has at least one, and preferably a plurality of knife elements 198 on its surface. The knife elements 198 are preferably configured to make a plurality of generally transverse direction cuts in the tube-forming composite web 188. The other roll 194 serves as an anvil member, and thus, may be referred to as anvil roll 194. The knife roll 192 and anvil roll 194 also define a nip 196 therebetween. After the cutting step, the individual tubes of absorbent material 22 are transported on a conveyor 200 for attachment to base pads 24 to form the sanitary napkin 20 of the present invention.

Other variations of the method described herein are possible. For example, it should be understood that the method of folding and bonding described herein is not limited to use in making a three dimensionally shaped tube of absorbent material for a compound sanitary napkin. This method can be used more broadly in making other types of three dimensionally-shaped absorbent articles from generally planar materials. The material or laminate of materials in issue can be folded and bonded in those locations where it is desirable for a portion of the folded web to assume a three dimensional shape, and can be left unfolded and unbonded in those locations where it is desirable for a portion of the material to remain more planar.

Figure 51:
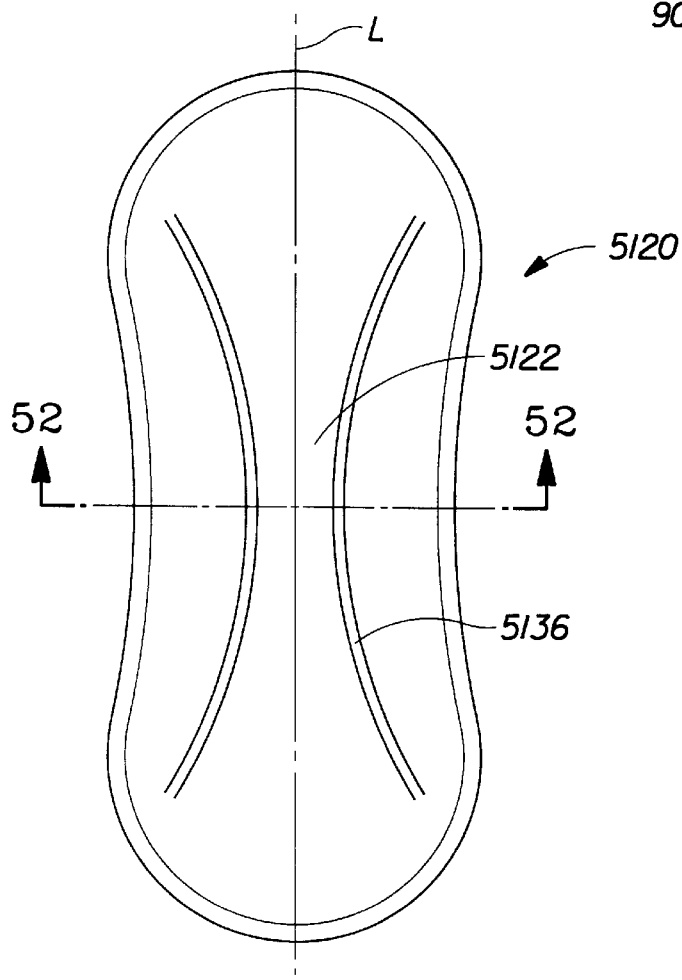
FIG. 51 is a simplified plan view of a sanitary napkin having a hump formed on its body-facing side by ultrasonic bonds that are fused to thermoplastic fibers in the absorbent material.
Figure 52:
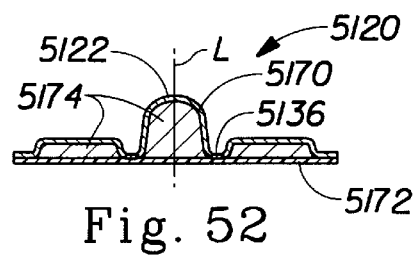
FIG. 52 is a cross-sectional view of the sanitary napkin shown in FIG. 51 taken along line 52—52 of FIG. 51.

It is also possible to maintain a hump or tube of absorbent material in place without bonding completely through the absorbent material. For example, FIGS. 51 and 52 show a three dimensionally-shaped sanitary napkin 5120 with a raised center portion 5122. The sanitary napkin 5120 comprises a topsheet 5170, a backsheet 5172, and an absorbent core 5174 that comprises at least some synthetic fibers. The synthetic fibers provide the absorbent core 5174 with improved integrity and provide a bondable material to attach the topsheet and/or backsheet to the absorbent core.

In one version of the embodiment shown in FIGS. 51 and 52, the absorbent core 5174 comprises between about 10–20% synthetic fibers homogeneously blended with airfelt and absorbent gelling material. The topsheet 5170 preferably comprises a DRI-WEAVE apertured film topsheet, and the backsheet 5172 preferably comprises a polyethylene film. The synthetic fibers in the absorbent core 5174 preferably comprise polyethylene to provide similar melting point properties to the topsheet and backsheet. Suitable commercially available synthetic fibers are PULPEX synthetic fibers. In the emboidment shown in FIG. 52, both the topsheet 5170 and backsheet 5172 are bonded to each other through the absorbent core 5174. However, in other embodiments, the absorbent core 5174 can be heated (such as by passing the sanitary napkin through a heat tunnel) to create a matrix of thermally bonded synthetic fibers into which it is possible to impress bond patterns to provide the sanitary napkin with a three dimensional shape without attaching the topsheet to the backsheet in the region of the bonds.

The embodiment shown in FIGS. 51 and 52 can be made using an ultrasonic die pattern in an hourglass shape with a recessed center (i.e., a pocket) to create the desired raised hump in the center of the sanitary napkin. The ultrasonic die and anvil roll can create heat and pressure to "weld" the topsheet and backsheet to the core area of the curvilinear channels. In other embodiments, less pressure can be used to weld only the topsheet 5170 to the absorbent core 5174. Such embodiments would rely on the synthetic fibers in the absorbent structure to maintain the core shape. The hourglass shape for the ultrasonic die can be used to provide better fit in the crotch area. The finished product is able to utilize the pressure created by the wearer's legs to actively "push" the center of the sanitary napkin into close contact with the wearer's body.

Blending synthetic fibers with any of the absorbent materials described herein in this manner may allow three dimensionally-shaped absorbent structures to be provided without bonding completely through the absorbent structure.

B. Attaching the Tube of Absorbent Material to the Base Pad to Form the Compound Sanitary Napkin.

FIG. 1 shows a compound sanitary napkin 20 having the tube of material 22 on the body-facing side thereof. To form the compound sanitary napkin 20, a sanitary napkin can serve as the panty protector (or "base pad") 24 and the tube of absorbent material wrapped by a topsheet 40 (or "primary menstrual pad") 22 is placed on top of the sanitary napkin 20 and attached thereto. Preferred sanitary napkins suitable for use as the base pad 24 are described above.

In a particularly preferred embodiment, the bonds 54 are located in the portion of the tube that will lie in the central region 32 of the sanitary napkin 20. In this preferred embodiment, this will form a tube which has the tri-lobal cross-sectional configuration described previously in conjunction with FIG. 2. In the preferred embodiment shown in FIG. 2, the portions 62 and 64 of the tube 22 that will lie in the end regions 28 and 30 of the sanitary napkin are preferably flattened and attached to the base pad 24.

The attachment of the tube 22 to the base pad 24 is preferably achieved by fusion bonding extensions 158 of the topsheet material at the ends of the tube to the base pad 24. In some preferred embodiments of such a compound sanitary napkin, there may also be attachment to the base pad 24 between the ends of the tube of absorbent material 22 and the base pad 24. The tube of the compound sanitary napkin can be attached to the base pad between its ends by any suitable attachment means, such as by adhesives.

The method of making the three dimensionally-shaped tube of absorbent material described herein provides numerous advantages. The method of the present invention involves very few steps and significantly less additional equipment, and does not require a delivery system that uses compressed air or a closed receptacle for containing the particulate material. In addition, because the particles are placed in a laminate structure, and are not blown or transferred from a delivery system, the result is a significant improvement in the control of the particle distribution. That is, the particles can be placed in precise locations within the tube of absorbent material. The method of the present invention also eliminates the need to re-meter (or measure) the quantity of the particulate material delivered to the tube of absorbent material.

The method of the present invention also provides the ability to maintain the characteristics of more than one layer of absorbent material relative to the other layers. For example, there could be two (or more) layers of absorbent material, such as absorbent foam, with different characteristics (e.g., pore size, hydrophilicity, etc.). For instance, the uppermost foam layer may have a larger pore size than the lower foam layer(s) to establish a capillary gradient from the outer portions of the tube of absorbent material to the inner portions of the tube of absorbent material. The method of the present invention is capable of forming one or more of these layers of foam material into strips or particulate material while maintaining the strips of particles of foam in their original vertical orientation. This preserves the desired relationship, unlike prior processes which involved air delivery systems. The prior processes would provide a random mixture of these particles instead.

In addition, the method of forming the absorbent material into particulate material described herein provides numerous other advantages. The method described herein can be used to provide the topsheet with a degree of extensibility due to the formation of a strainable network of regions therein by the patterned rolls. The formation of a strainable network region in a material to provide the same with extensibility is discussed in greater detail in the Chappell, et al. patent. The method of the present invention can also be used to provide the topsheet with added softness due to the impression of the patterned surfaces therein. The method described herein can also be used to provide the topsheet with increased flexibility due to the plurality of additional bending axes imparted into the topsheet by the ridges and valleys on the patterned rolls. Further, the method described herein may also provide the advantage of improving the integrity between the layers of the composite web.

In addition, using this method, the absorbent articles may be very easily shaped by conventional folding appartuses, and the shapes and/or dimensions of the tube of absorbent material may be varied (for example, if necessary to accommodate consumer preferences in different geographies) by changing tooling rather than changing the basic process.

In other embodiments, the different features of any of the embodiments described herein can be combined to produce still other embodiments. For example, a sanitary napkin can be provided which has a tube of absorbent material in a tri-lobal cross-sectional configuration as shown in FIGS. 1 and 2, but which is wholly integrated into the base pad, and forms a part of the absorbent core of the base pad similarly to the mushroom shaped structure shown in FIGS. 26–28.

One example of such a sanitary napkin can be formed by forming a laminate arranged from top to bottom of: topsheet material (e.g. DRI-WEAVE apertured film), a layer of secondary topsheet material (e.g. P-9 nonwoven material), absorbent foam material, and another layer of secondary topsheet material. The longitudinal central region of the laminate thus formed is preferably subjected to the SELFing process, but the laterally outboard portions are preferably not SELFed. The SELFed portion will form a raised absorbent hump with softer, body conforming properties. The entire laminate is then folded and bonded similarly to the tri-lobal structure shown in FIG. 2, only the longitudinal side margins of the folded web do not extend upward into the central lobe 34 and a separate topsheet is not provided for the tube thus formed. Instead, the longitudinal side margins extend up to the bond area, and are folded back downward and laterally outward as in the case of the mushroom shaped structure shown in FIG. 27 to form the absorbent core of the base pad. A backsheet can then be added and the folded and bonded laminate can be cut in the desired shape to complete the formation of the sanitary napkin.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention.

What is claimed is:

1. A method of making a shaped tube of absorbent material for an absorbent article, said method comprising the steps of:
   (a) providing a web of absorbent material, said web of absorbent material having a first surface and an opposed second surface;
   (b) providing a cover for said web of absorbent material;
   (c) at least partially covering the first and second surfaces of said web of absorbent material with said cover to form a covered web of absorbent material;
   (d) forming said covered web of absorbent material into a tube of absorbent material;
   (e) autogenously bonding one portion of said cover to an opposing portion of said cover while displacing said absorbent material to form at least one bond, forming the shaped tube.

2. The method of claim 1 wherein step (d) comprises folding said covered web of absorbent material.

3. The method of claim 1 wherein said absorbent material comprises an absorbent foam.

4. The method of claim 1 further comprising a step of forming said absorbent material into a plurality of particles prior to the autogenous bonding step (e).

5. The method of claim 3 wherein said absorbent foam comprises a plurality of pieces which are generally in the shape of parallelepipeds.

6. A method of making a shaped tube of absorbent material for an absorbent article, said method comprising the steps of:
   (a) providing a web of absorbent material, said web of absorbent material having a length, a width, a longitudinal centerline oriented in the direction of the length of said web of absorbent material, a first surface and an opposed second surface;
   (b) providing a cover for the first and second surfaces of said web of absorbent material;
   (c) at least partially covering the first and second surfaces of said web of absorbent material with said cover to form a tube-forming composite web of absorbent material having longitudinal side margins;
   (d) folding said tube-forming composite web at least once with folds defining fold lines that are arranged about the longitudinal centerline of the web of absorbent material; and
   (e) autogenously bonding a portion of said cover that covers said first surface of said web of absorbent material to a portion of said cover that covers an opposing portion of the second surface of said web of absorbent material, forming the shaped tube.

7. The method of making a shaped tube of absorbent material for an absorbent article comprising the steps of:
   (a) providing a web of absorbent material, said web of absorbent material having a length, a width, a longitudinal centerline oriented in the direction of the length of said web of absorbent material, a first surface and an opposed second surface;
   (b) providing a cover for the first and second surfaces of said web of absorbent material;
   (c) at least partially covering the first and second surfaces of said web of absorbent material with said cover to form a tube-forming composite web of absorbent material having longitudinal side margins;
   (d) folding said tube-forming composite web at least once with folds defining fold lines that are arranged about the longitudinal centerline of the web of absorbent material; folding the longitudinal side margins of said composite web inward toward the longitudinal centerline about a first longitudinally-oriented fold line to form a C-folded structure; folding the composite web inward about the longitudinal centerline so that the longitudinal side margins of said folded composite web are brought adjacent to each other; and
   (e) autogenously bonding a portion of said cover that covers said first surface of said web of absorbent material to a portion of said cover that covers an opposing portion of the second surface of said web of absorbent material, forming the shaped tube.

8. A method of making a compound sanitary napkin, said method comprising the steps of:
   (a) providing a shaped of absorbent material tube made by the method of claim 6, said tube forming composite having a pair of end portions;
   (b) providing a base pad;
   (c) splaying out the ends of the tube; and
   (d) joining said tube to said base pad.

* * * * *